(12) United States Patent
Dahlen et al.

(10) Patent No.: US 7,632,647 B2
(45) Date of Patent: Dec. 15, 2009

(54) USE OF B-TYPE NATRIURETIC PEPTIDE AS A PROGNOSTIC INDICATOR IN ACUTE CORONARY SYNDROMES

(75) Inventors: Jeffrey R. Dahlen, San Diego, CA (US); Kenneth F. Buechler, San Diego, CA (US); Gunars E. Valkirs, Escondido, CA (US)

(73) Assignee: Biosite Incorporated, San Diego, CA (US)

( * ) Notice: Subject to any disclaimer, the term of this patent is extended or adjusted under 35 U.S.C. 154(b) by 1755 days.

(21) Appl. No.: 09/835,298

(22) Filed: Apr. 13, 2001

(65) Prior Publication Data

US 2003/0022235 A1 Jan. 30, 2003

(51) Int. Cl.
*G01N 33/53* (2006.01)
(52) U.S. Cl. .................. 435/7.1; 435/4; 435/7.92
(58) Field of Classification Search ............ 435/7.1, 435/7.92, 7.93, 7.94, 969, 970, 973, 975; 436/514, 518, 528, 530, 807, 808, 810; 422/60, 422/61
See application file for complete search history.

(56) References Cited

U.S. PATENT DOCUMENTS

| | | | |
|---|---|---|---|
| 5,206,140 A | 4/1993 | Marder et al. | |
| 5,290,678 A * | 3/1994 | Jackowski | 435/7.4 |
| 5,352,587 A | 10/1994 | Chang et al. | |
| 5,422,393 A | 6/1995 | Bricker et al. | |
| 5,480,792 A | 1/1996 | Buechler et al. | |
| 5,525,524 A | 6/1996 | Buechler et al. | |
| 5,580,722 A | 12/1996 | Foulkes et al. | 435/6 |
| 5,604,105 A | 2/1997 | Jackowski | |
| 5,631,171 A | 5/1997 | Sandstrom et al. | |
| 5,679,526 A | 10/1997 | Buechler et al. | |
| 5,747,274 A | 5/1998 | Jackowski | |
| 5,786,163 A | 7/1998 | Hall | 435/7.92 |
| 5,795,725 A | 8/1998 | Buechler et al. | |
| 5,824,799 A | 10/1998 | Buechler et al. | |

(Continued)

FOREIGN PATENT DOCUMENTS

WO WO91/09627 7/1991

(Continued)

OTHER PUBLICATIONS

Newby et al., "Bedside Multimarker Testing for Risk Stratification in Chest Pain Units; The Chest Pain Evaluation by Creatine Kinase-MB, Myoglobin, and Troponin I (Checkmate) Study" Circulaton, (Apr. 10, 2001); 103: pp. 1832-1837.*

(Continued)

*Primary Examiner*—Ann Y Lam
(74) *Attorney, Agent, or Firm*—Wilson Sonsini Goodrich & Rosati, PC

(57) ABSTRACT

The present invention relates to materials and procedures for evaluating the prognosis of patients suffering from acute coronary syndromes. In particular, the level of BNP, or a marker related to BNP, in a patient sample, alone or in combination with one or more other prognostic markers, provides prognostic information useful for predicting near-term morbidity and/or mortality across the entire spectrum of acute coronary syndromes, including unstable angina, non-ST-elevation non-Q wave myocardial infarction, ST-elevation non-Q wave MI, and transmural (Q-wave) MI.

8 Claims, 7 Drawing Sheets

U.S. PATENT DOCUMENTS

| | | | |
|---|---|---|---|
| 5,851,776 | A | 12/1998 | Valkirs |
| 5,885,527 | A | 3/1999 | Buechler |
| 5,922,615 | A | 7/1999 | Nowakowski et al. |
| 5,939,272 | A | 8/1999 | Buechler et al. |
| 5,947,124 | A | 9/1999 | Buechler et al. |
| 5,955,377 | A | 9/1999 | Maul et al. |
| 5,985,579 | A | 11/1999 | Buechler et al. |
| 6,019,944 | A | 2/2000 | Buechler |
| 6,113,855 | A | 9/2000 | Buechler |
| 6,117,644 | A | 9/2000 | DeBold ...................... 435/7.1 |
| 6,143,576 | A | 11/2000 | Buechler |
| 6,147,688 | A | 11/2000 | Clair |
| 6,156,521 | A | 12/2000 | Buechler et al. |
| 6,171,870 | B1 * | 1/2001 | Freitag ...................... 436/518 |
| 6,309,888 | B1 | 10/2001 | Holvoet et al. |
| 6,461,828 | B1 | 10/2002 | Stanton et al. |
| 6,627,457 | B2 | 9/2003 | Pandian et al. |
| 6,670,138 | B2 | 12/2003 | Gonzalez-Zulueta et al. |
| 6,756,483 | B1 | 6/2004 | Bergmann et al. |

FOREIGN PATENT DOCUMENTS

| | | |
|---|---|---|
| WO | WO 00/22439 | 4/2000 |
| WO | WO 02/083913 | 10/2002 |

OTHER PUBLICATIONS

Antman et al., "Cardiac-specific Troponin I Levels to Predict the Risk of Mortality in Patients with Acute Coronary Syndromes", The New England Journal of Medicine, (1996), pp. 1342-1349, vol. 335, No. 18.*

Richards et al., ["Neuroendocrine prediction of left ventricular function and heart failure after acute myocardial infarction", Heart, (1999); 81: 114-120].*

Huttunen et al., Coregulation of neurite outgrowth and cell survival by amphoterin and S100 proteins through receptor for advanced glycation end products (RAGE) activation. The Journal of Biological Chemistry, 275:40096-4010, 2000.

Mussack et al., Early cellular brain damage and systemic inflammatory response after cardiopulmonary resuscitation or isolated severe head trauma: a comparative pilot study on common pathomechanisma.

Yakoviev et al., Activation of CPP32-Like caspases contributes to neuronal apoptosis and neurological dysfunction after traumatic brain injury. The Journal Neuroscience, 17(19):7415-724, 1997.

International Search Report for international application No. PCT/US04/26984.

Notice of References Cited, PTO-892, Part of Paper No. 20041202 from U.S. Appl. No. 10/225,082, filed Aug. 20, 2002.

Alexander et al., "30-Day and 6-Month Nortality in Proportional to Magnitudr of Peak Creatine Kinase Elevation in the Non-ST-elevation Acute Coronary Syndromes," Circulation (Supp.), 1998, p. I-629.

Antman et al., "Cardiac-Specific Troponin I Levels to Predict the Risk of Mortality in Patients with Acute Coronary Syndromes," The New England Journal of Medicine, 1996, p. 1342-1349, vol. 335, No. 18.

Antman et al., "Enoxaparin Prevents Death and Cardiac Ischemic Events in Unstable Angina/Non-Q-Wave Myocardial Infarction," Circulation, 1999, p 1593-1601, vol. 100.

Arakawa et al., "Relationship Between Plasma Level of Brain Natriuretic Peptide and Myocardial Infarct Size," Cardiology, 1994, p. 334-340, vol. 85.

Arakawa et al., "Plasma Brain Natriuretic Peptide Concentrations Predict Survival After Acute Myocardial Infraction," JACC, Jun. 1996, p. 1656-1661, vol. 27, No. 7.

Berger et al., "B-Type Natriuretic Peptides (BNP and PRO-BNP) Predict Longterm Survival in Patients with Advanced Heart Failure Treated with Atenolol," Journal of the Heart and Lung Transplantation, 2001, p. 251, vol. 20, No. 2.

Braunwald et al., "Unstable Angina: Diagnosis and Management," Clinical Practice Guideline No. 10 (amended), AHCRP Publication No. 94-0602, Rockville, MD: Department of Health and Human Services, 1994.

Cannon et al., "Invasive Versus Conservative Strategies in Unstable Angina and Non-Q-Wave Myocardial Infarction Following Treatment with Tirofiban: Rationale and Study Design of the International TACTICS-TIMI18 Trial," Am. J. Cardiology, 1998, p. 731-736, vol. 82.

Cannon et al., "Oral Glycoprotein llB/llla Inhibition with Orgofiban in Patients with Orbofiban in Patients with Unstable Coronary Syndromes (OPUS-TIMI 16) Trial," Circulation, 2000, p. 149-156, vol. 102.

Cheng et al, "A Rapid Bedside Test for B-Type Peptide Predicts Treatment Outcomes in Payients Admitted for Decompensated Heart Failure: A pilot Study," Journal of the American College of Cardiology, 2001, p. 386-391, vol. 37, No. 2.

Dao et al., "Utility of B-Type Natriuretic Peptide in the Diagnosis of Congestive Heart Failure in an Urgent- Care Setting," Journal of the American College of Cardiology, 2001, p. 379-385, vol. 37, No. 2.

Darbar et al., "Diagnostic Value of B-Type Natriuretic Peptide Concentrations in Patients with Acute Myocardial Infarction," Am. J. Cardiology, 1996, p. 284-287, vol. 78.

Fischer et al., "Evaluation of a New, Rapid Bedside Test for . . . ," Clinical Chemistry, 2001, p. 591-594, vol. 47, No. 3.

Grayburn et al., "Perflenapent Emulsion (EchoGen®): A New Long-Acting Phase-Shift Agent for Contrast Echocardiology," Clinical Cardiology, 1997, p. 1-12-1-18, vol. 20 (Supp l).

Hama et al., "Rapid Ventricular Induction of Brain Natriuretic Peptide Gene Expression in Experimental Acute Mycocardial Infarction," Circulation, 1995, p. 1558-1564, vol. 92.

Hamm et al., "Benefit of Abciximab in Patients with refractory Unstable Angina in Relation to serum Troponin T Levels," New England Journal of Medicine, 1999, p. 1623-1629, vol. 340, No. 21.

Horio et al., "Serial Changes in Atrial and Brian Natriuretic Peptides in Patients with Acute Myocardial Infarction Treated with early Coronary Angioplasty," American Heart Journal, 1993, p. 293-299, vol. 126.

Hunt et al., "The Amino-Terminal Portion of Pro-Brain Natriuretic Peptide (Pro-BNP) Circulates in Human Plasma," Biochemical and Biphysical Research Communications, 1995, p. 1175-1183, vol. 214, No. 3.

Kikuta et al., "Increased Plasma Levels of B-Type Natriuretic Peptide in Patients with Unstable Angina," American Heart Journal, 1996, p. 101-107, vol. 132, No. 1.

Klootwijk et al., "Acute Coronary Syndromes: Diagnosis," The Lancet, Jun. 1999, p. 1109-1113, vol. 132.

Kyriakides et al., "Brain Natriuretic Peptide Increases Acutely and Much More Prominently than Atrial Natriuretic Peptide during Coronary Angioplasty," Clinical Cardiology, 2000, p. 285-288, vol. 23.

Llodyd-Jones et al., "Electrocardiographic and Clinical Predictors of Acute Myocardial Infarction in Patients with Unstable Angina Pectoris," Am. J. Cardiology, 1998, p. 1182-1186, vol. 81.

Marumoto et al., "Increased Secretion of Atrial and Brain Natriuretic Peptides During Acute Myocardial Ischaemia Induced by Dynamic Exercise in Patients with Angina Pectoris," Clinical Science, 1995, p. 551-556, vol. 88.

Morrow et al., "C-Reactive Protein Is a Potent Predictor of Mortality Independently of and in Combination With Troponin T in Acute Coronary Syndromes: A TIMI 11A Substudy," JACC, Jun. 1998, p. 1460-1465, vol. 31, No. 7.

Morrow et al., "Cardiac Troponin I for Stratification of early Outcomes and the efficacy of Enoxaparin in Unstable Angina: A TIMI-11B Substudy," JACC, 2000, p. 1812-1817, vol. 36, No. 6.

Motwani et al., "Plasma Brain Natriuretic Peptide as an Indicator for Angiotensin-converting-enzyme Inhibition After Myocardial Infraction," The Lancet, 1993, p. 1109-1113, vol. 341.

Nagaya et al., "Plasma Brain Natriuretic Peptide is a Biochemical Marker for the Prediction of Progressive Ventricular Remolding after Acute Myocardial Infarction," American heart Journal, 1998, p. 21-28, vol. 135.

Nyman et al., "Very Early Risk Stratification by Electrocardiogram at Rest in Men with Suspected Unstable Coronary Heart Disease," Journal of Internal Medicine, 1993, p. 293-301, vol. 234.

Omland et al., "Plasma Brain Natriuretic Peptide as an Indicator of Left Ventricular Systolic Function and Long-term Survival After Acute Myocardial Infarction," Circulation, 1996, p. 1063-1969, vol. 93.

Omland et al, "Plasma Cardiac Natriuretic Peptide Determination as a Screening Test for the Detection of Patients with Mid Left Ventricular Impairment," Heart, 1996, p. 232-237, vol. 76.

Patel et al., "Early Continuous ST Segment Monitoring in Unstable Angina: Prognostic Value Additional to the Clinical Characteristics and the Admission Electrocardiogram," Heart, 1996, p. 222-228, vol. 75.

Patel et al., "The Importance of Early Risk Stratification Using Continuous ST Segment Monitoring," European Heart Journal, 1998, p. 240-249, vol. 19.

Richards et al., "Plasma N-Terminal Pro-Brain Natriuretic Peptide and Adrenomedullin," Circulation, 1998, p. 1921-1929, vol. 97.

Richards et al., "Neuroendocrine Prediction of Left Ventricular Function and Heart Failure After Acute Myocardial Infarction," Heart, 1999, p. 114-120, vol. 81.

Ridker et al., "Inflammation, Pravastatin, and the Risk of Coronary Events After Myocardial Infarction in Patients with Average Cholesterol Levels," Circulation, 1998, p. 839-844, vol. 98.

Savonitto et al., "Prognostic Value of the Admission Electrocardiogram in Acute Coronary Syndromes," JAMA, 1998, p. 707-713, vol. 281.

Stein et al., "Natriuretic Peptides: Physiology, Therapeutic Potential, and Risk Stratification in Ischemic Heart Disease," American heart Journal, 1998, p. 914-923, vol. 135.

Talwar et al., "Profile of Plasma N-terminal proBNP Following Acute Myocardial Infarction," Europen Heart Journal, 2000, p. 1514-1521, vol. 21.

Talwar et al., "Plasma N-terminal Pro-Brain Natriuretic Peptide and Cardiotrophin 1 are raised in Unstable Angina," Heart, 2000, p. 421-424, vol. 84.

Tateishi et al., "Transient Increase in Plasma Brain (B-Type) Natriuretic Peptide After Percutaneous Transluminal Coronary Angioplasty," Clinical Cardiology, 2000, p. 776-780, vol. 23.

Tateyama et al., "Concentrations and Molecular Forms of Human Brain Natriuretic Peptide in Plasma," Biochemical and Biophysical Research Communications, 1992, p. 760-767, vol. 185, No. 2.

Theroux et al., "Acute Coronary Syndromes," Circulation, 1998, p. 1195-1206, vol. 97.

Throughton et al., "Treatment of Heart Failure Guided by Plasma Aminoterminal Brain Natriuretic Peptide (N-BNP) Concentrations," The Lancet, 2000, p. 1126-1130, vol. 355.

Van Veldhuisen et al., "High Versus Low Dose ACE Inhibition in Chronic Heart Failure," JACC, 1998, p. 1811-1818, vol. 32, No. 7.

Weise et al., "Gene Expression of Brain Natriuretic Peptide in Isolated Atrial and Ventricular Human Myocardium," Circulation, 2000, p. 3074-3079, vol. 102.

Yasue et al., "Localization and Mechanism of Secretion of B-Type Natriuretic Peptide in Comparison with Those of A-Type Natriuretic Peptide in Normal Subjects and Patients with Heart failure," Circulation, 1998, p. 195-203, vol. 90.

Yoshimura et al., "Different Secretion Patterns of Atrial Natriuretic Peptide and Brain Natriuretic Peptide in Patients with Congestive Heart Failure," Circulation, 1993, p. 464-469, vol. 87.

Yusuf et al., "Variations Between Countries in Invasive Cardiac Procedures and Outcomes in Patients with Suspected Unstable Angina or Myocardial Infarction without Initial ST Elevation," The Lancet, 1998, p. 507-514, vol. 352.

Saady et al., "Left appendage: structure function, and role in thromboembolism," Heart, 1999, pp. 547-555, vol. 82.

Party Stanton Proofs of Invention for Interference 105, 167.

Declaration of George Jackowski, Interference No. 105, 167.

Declaration of Dr. A. Mark Richards, Interference No. 105, 167.

Declaration of Eric Stanton, Interference No. 105, 167.

Al-Ahmad et al., Reduced Kidney Function and Anemia as Risk Factors for Mortality in Patients With Left Ventricular Dysfunction, Journal of the American College of Cardiology, Oct. 2001, pp. 955-962, vol. 38, No. 4, Elsevier Science Inc.

Altemose et al., Altered Myocardial Phenotype After Mechanical Support in Human Beings with Advanced Cardiomyopathy, The J. Heart and Lung Transplantation, Jul. 1997, pp. 785-773, vol. 16, No. 7.

Ando et al., Plasma Concentrations of Atrial, Brain, and C-type Natriunetic Peptides and Endothelin-1 in Patients With Chronic Respiratory Diseases, CHEST, Aug. 1996, pp. 462-468, vol. 110, No. 2.

Apple et al., Myocardial Infarction Redefined: Role of Cardiac Troponin Testing, Clinical Chemistry, 2001, pp. 377-379, vol. 47, No. 3.

Arakawa et al., Relationship between Plasma Level of Brain Natriuretic Peptide and Myocardial Infarct Size, Cardiology, Nov. 1994, pp. 334-340, vol. 85, No. 5.

Arakawa et al., Plasma Brain Natiuretic Peptide Concentrations Predict Survival After Acute Myocardial Infarction, J. Am. Coll. Cardiol., Jun. 1996, pp. 1656-1661, vol. 27, No. 7, Elsevier Science Inc.

Ballermann, Amer. J. of Physiology, Jan. 1988, pp. F159-F163, vol. 254, No. 1, Part 2 of Two Parts, The American Physiological Society.

Bellorini et al., Interest of BNP and Troponin in the Management of Cardiologic Emergency, J. of European Society of Cardiology, Sep. 1-5, 2001, p. 518, vol. 22.

Blomkalns et al., Markers and the Initial Triage and Treatment of Patients with Chest Pain, Cardiovascular Toxicology, 2001, pp. 111-115, vol. 1, No. 2, Humana Press.

Bolli et al., Myocardial Protection at a Crossroads: The Need for Translation Into Clinical Therapy, Circulation Research, Jul. 23, 2004, pp. 125-134.

Boomsma et al., Plasma A- and B-type Natriuretic Peptides: Physiology, Methodology and Clinical Use, Cardiovascular Research, 2001, pp. 442-449, vol. 51, Elsevier.

Bruccoleri et al., Brain Natriuretic Peptide in Patients with Acute Myocardial Infarction and Hypertension, Clin Chem Lab Med, Jun. 1999, Special Supplement, p. S440, vol. 37.

De Bruyne et al., Prolonged QT Interval Predicts Cardiac and All-Cause Mortality in the Elderly, Eur Heart J, Feb. 1999, pp. 278-284, vol. 20, No. 4.

Bürgisser et al., Human Cardiac Plasma Concentrations of Atrial Natriuretic Peptide Quantified by Radioreceptor Assay, Biochemical and Biophysical Research Communications, Dec. 31, 1985, pp. 1201-1209, vol. 133, No. 3, Academic Press, Inc.

Cameron et al., Natriuretic Peptide System in Fetal Heart and Circulation, Journal of Hypertension, 2002, pp. 801-803, vol. 20, No. 5.

Cannon et al., Oral Glycoprotein llb/llla Inhibition With Orbofiban in Patients With Unstable Coronary Syndromes (OPUS-TIMI 16) Trial, Circulation, Jul. 11, 2000, pp. 149-156.

Cannon et al., ACC Clinical Data Standards, American College of Cardiology Key Data Elements and Definitions for Measuring the Clinical Management and Outcomes of Patients with Acute Coronary Syndromes, J. Am. Coll. Cardiol., Dec. 2001, pp. 2114-2130, vol. 38, No. 7, Elsevier Science Inc.

Cantin et al., The Heart and the Atrial Natriuretic Factor, Endocrine Reviews, Spring 1985, pp. 107-127, vol. 6, No. 2.

Chen et al., The Natriuretic Peptides in Heart Failure: Diagnostic and Therapeutic Potentials, Proceedings of the Assoc of American Physicians, Sep./Oct. 1999, pp. 406-416, vol. 111, No. 5.

Chu et al., A Review of Clinically Relevant Cardiac Biochemical Markers, Wisconsin Medical Journal, 2002, pp. 40-48, vol. 101, No. 3.

Clerico et al., Diagnostic Accuracy and Prognostic Relevance of the Measurement of Cardiac Natriuretic Peptides: A Review, Clinical Chemistry, 2004, pp. 33-50, vol. 50, No. 1.

Collinson et al., Measurement of Cardiac Troponins, Am Clin Biochem, Sep. 2001, pp. 423-449, vol. 38, The Royal Society of Medicine Press.

Croal et al., Brain Natriuretic Peptide and Cardiac Troponin I as Markers of Doxorubicin Cardiotoxicity, Journal of the American Society of Hematology, Nov. 16, 2000, Part 2 of 2 Parts, pp. 239b, vol. 96, No. 11.

Croal et al., Cardiac Troponin I and Brain Natriuretic Peptide as Markers of Doxorubicin Cardiotoxicity, Clinical Chemistry, 2001, Supplement, p. A149, vol. 47, No. 6.

Darbar et al., Diagnostic Value of B-Type Natriuretic Peptide Concentrations in Patients With Acute Myocardial Infarction, The American Journal of Cardiology, Aug. 1, 1996, pp. 284-287, vol. 78.

Davidson et al., C-Type Natriuretic Peptide, An Endogenous Inhibitor of Vascualr Angiotensin-Converting Enzyme Activity, Circulation, 1996, pp. 1155-1159, vol. 93.

Davidson et al., Comparison of Atrial Natriuretic Peptide, B-Type Natriuretic Peptide, and N-Terminal Proatrial Natriuretic Peptide as Indicators of Left Ventricular Systolic Dysfunction, The American Journal of Cardiology, Apr. 15, 1996, pp. 828-831, vol. 77.

De Bold A.J., Atrial Natriuretic Factor: A Hormone Produced by the Heart, Science, Nov. 15, 1985, pp. 767-770, vol. 230.

De Lemos et al., The Prognostic Value of B-Type natriuretic Peptide in Patients with Acute Coronary Syndromes, N. Engl. J. Med., Oct. 4, 2001, pp. 1014-1021, Vol. 345, No. 14, Massachusetts Medical Society.

De Lemos et al., Combining Natriuretic Peptides and Necrosis Markers in the Assessment of Acute Coronary Syndromes, Reviews in Cardiovascular Medicine, 2003, pp. S37-S46, vol. 4, Supp. 4.

Domanski et al., A Comparative Analysis of the Results From 4 Trials of βBlocker Therapy for Heart Failure: Best, CIBIS-II, Merit-HF, and CORPERNICUS, J. of Cardiac Failure, Oct. 2003, pp. 354-363, vol. 9, No. 5.

Donaldson et al., Cardiac Troponin Levels in Patients with Impaired Renal Function, Hospital Medicine, Feb. 2001, pp. 86-89, vol. 62, No. 2.

Fonarow et al., Combining Natriuretic Peptides and Necrosis Markers in Determining Prognosis in Heart Failure, Reviews in Cardiovascular Medicine, 2003, pp. S20-S28, vol. 4, Suppl. 4.

Freemantle et al., Composite Outcomes in Randomized Trials; Greater Precision But With Greater Uncertainty? JAMA, May 21, 2003, pp. 2554-2559, vol. 289, No. 19 (Reprinted).

Goldacre et al., Multiple-cause Coding of Death from Myocardial Infarction: Population-Based Study of Trends in Death Certificate Data, Journal of Public Health Medicine, Mar. 2003, pp. 69-71, vol. 25, No. 1, Oxford University Press, Great Britain.

Gutkowska et al., Radioreceptor Assay for Atrial Natriuretic Factor, Analytical Biochemistry, Jan. 1988, pp. 100-106, vol. 168, No. 1, Academic Press, Inc.

Hampton et al., Achieving Appropriate Endpoints in Heart Failure Trials: the PRIME-II Protocol, The European Journal of Heart Failure, 1999, pp. 89-93, vol. 1.

Hammerer-Lercher et al., Head-to-Head Comparison of N-terminal Pro-brain Natriuretic Peptide, Brain Natriuretic Peptide and N-terminal Pro-atrial Natriuretic Peptide in Diagnosing Left Ventricular Dysfunction, Clinica Chimica Acta, 2001, pp. 193-197, vol. 310.

Holmes, Jr. et al., Cause of Death Analysis in the NHLBI PTCA Registry: Results and Considerations for Evaluating Long-Term Survival After Coronary Interventions, J. Am. Coll. Cardiol., Oct. 1997, pp. 881-887, vol. 30, No. 4, Elsevier Science Inc.

Horio et al., Serial Changes in Atrial and Brain Natriuretic Peptides in Patients with Acute Myocardial Infarction Treated with Early Coronary Angioplasty, American Heart Journal, Aug. 1993, pp. 293-299, vol. 126, No. 2.

Hunt et al., Bioactivity and Metabolism of C-Type Natriuretic Peptide in Normal Man, J Clin Endocrinol Metab, 1994, pp. 1428-1435, vol. 78, No. 6.

Hunt et al., Differing Biological Effects of Equimolar Atrial and Brain Natriuretic Peptide Infusions in Normal Man, J Clin Endocrinol Metab, 1996, pp. 3871-3876, vol. 81, No. 11.

Hwang et al., Analysis of Expressed Sequence Tags from a Fetal Human Heart cDNA Library, Genomics, 1995, pp. 293-298, vol. 30.

Ikram et al., An Ovine Model of Acute Myocardial Infarction and Chronic Left Ventricular Dysfunction, Angiology, Aug. 1997, vol. 48, No. 8, 1 page abstract retrieved on-line on Jul. 27, 2004.

Ishii et al., Risk Stratification Using Cardiac Troponin T in Patients with End-Stage Renal Disease, Supplement to Circulation, Journal of the American Heart Association, Nov. 7-10, 1999, Abstracts from the 72$^{nd}$ Scientific Sessions, p. I-177.

Ishii et al., Early Risk Stratification Using Cardiac Troponin T and Brain Natriuretic Peptide in Patients with Congestive Heart Failure, Supplement to Circulation, Journal of the American Heart Association, Nov. 7-10, 1999, Abstracts from the 72$^{nd}$ Scientific Sessions, p. I-679.

Ishii et al., Risk Stratification Using Serum Concentrations of Cardiac Troponin T in Patients with end-stage Renal Disease on Chronic Maintenance Dialysis, Clinica Chimica Acta, 2001, pp. 69-79, vol. 312.

Ishii et al., Risk Stratificatin Using a Combination of Cardiac Troponin T and Brain Natriuretic Peptide in Patients Hospitalized for Worsening Chronic Heart Failure, The American Journal of Cardiology, Mar. 15, 2002, pp. 691-695, vol. 89.

Itoh et al., Occurrence of a Novel Cardiac Natriuretic Peptide in Rats, Biochemical and Biophysical Research Communications, Jun. 15, 1989, pp. 732-739, vol. 161, No. 2.

Jaffe A.S., New Standard for the Diagnosis of Acute Myocardial Infarction, Cardiology in Review, 2001, p. 318-322, vol. 9, No. 6.

Jancin B., Rapid test Helps Identify Cause of Dyspnea—Point-of-Care Brain Natriuretic Peptide Immunoassay, [on-line]. Retrieved from the Internet Oct. 18, 2004: <URL: http://www.findarticles.com/p/articles/mi_m0BJI/is_9_30/ai_63125276/..., 2 pages.

Jourdain et al., B Type Natriuretic Peptide and Cardiac Troponin I in Acute Chest Pain, Oct. 21-24, 2001, Advances in Coronary Artery Disease, Proceedings of the 4$^{th}$ International Congress on Coronary Artery Disease, pp. 509-515.

Karras et al., Serum Markers in the Emergency Department Diagnosis of Acute Myocardial Infarction, Emergency Medicine Clinics of North America, May 2001, pp. 321-337, vol. 19, No. 2, W.B. Saunders Company.

Kelly et al., Are Natriuretic Peptides Clinically Useful as Markers of Heart Failure?, Ann. Clin. Biochem., 2001, pp. 94-102, vol. 38.

Klinger et al., C-type Natriuretic Peptide Expression and Pulmonary Vasodilation in Hypoxia-adapted Rats, Am. J. Physiol, vol. 275 (Lung Cell Mol Physiol), 1998, pp. L645-L652.

Lainchbury et al., Brain Natriuretic Peptide and N-Terminal Brain Natriuretic Peptide in the Diagnosis of Heart Failure in Patients With Acute Shortness of Breath, J. Am. Coll. Cardiol., Aug. 20, 2003, pp. 728-735, vol. 42, No. 4, Elsevier Inc.

Laragh J.H., Atrial Natriuretic Hormone, the Renin-Aldosterone Axis, and Blood Pressure-electrolyte Homeostasis, The New England Journal of Medicine, Nov. 21, 1985, pp. 1330-1340, vol. 313, No. 21, Massachusetts Medical Society.

Cibis-II Investigators and Committees, The Cardiac Insufficiency Bisprolol Study II (CIBIS-II): A Randomised Trial, The Lancet, Jan. 2, 1999, pp. 9-13, vol. 353.

Li et al., Greater Frequency of Increased Cardiac Troponin T Than Increased Cardiac Troponin I in Patients with Chronic Renal Failure, Clinical Chemistry, 1996, pp. 114-115, vol. 42, No. 1.

Liew et al., A Catalogue of Genes in the Cardiovascular System as Identified by Expressed Sequence Tags, Proc. Natl. Acad. Sci. USA, Oct. 1994, pp. 10645-10649, vol. 91.

Lindahl, B., N. Engl. J. Med., Nov. 22, 2001, pp. 1579-1580, vol. 345, No. 21, Massachusetts Medical Society.

Luchner et al., Differential Atrial and Ventricular Expression of Myocardial BNP During Evolution of Heart Failure, pp. H1684-H1689 (1998).

Maeda et al., High levels of Plasma Brain Natriuretic Peptide and Interleukin-6 After Optimized Treatment for Heart Failure are Independent Risk Factors for Morbidity and Mortality in Patients with Congestive Heart Failure, J. Am. Coll. Cardiol., Nov. 1, 2000, pp. 1587-1593, vol. 36, No. 5, Elsevier Science Inc.

Maisel A., Cardiac Biomarkers Aid in Diagnosing Ischemia and Heart Failure, CVR&R, Apr. 2001, pp. 217-222, vol. 22, No. 4.

Manning et al., The Protein Kinase Complement of the Human Genome, Science, Dec. 6, 2002, pp. 1912-1916 and 1933-1934, vol. 298.

Mäntymaa et al., Atrial Stretch Induces Rapid Increase in Brain Natriuretic Peptide But Not in Atrial Natriuretic Peptide Gene Expression In Vitro, Endocrinology, 1993, pp. 1470-1473, vol. 133, No. 3.

Martin et al., Estimation of Myocardial Infarction Mortality from Routinely Collected Data in Western Australia, J. Chron. Dis., 1987, pp. 661-669, vol. 40, No. 7, Great Britain.

McCullough et al., Performance of Multiple Cardiac Biomarkers Measured in the Emergency Department in Patients with Chronic Kidney Disease and Chest Pain, Acad. Emerg. Med., Dec. 2002, pp. 1389-1396, vol. 9, No. 12.

McCullough et al., B-Type Natriuretic Peptide and Renal Function in the Diagnosis of Heart Failure: An Analysis From the Breathing Not Property Multinational Study, American Journal of Kidney Diseases, Mar. 2003, pp. 571-579, vol. 41, No. 3.

McCullough et al., Risks Associated With Renal Dysfunction in Patients in the Coronary Care Unit, J. Am. Coll. Cardiol., Sep. 2000, pp. 679-684, vol. 36, No. 3, Elsevier Science Inc.

McCullough P.A., Beyond Serum Creatinine: Defining the Patient with Renal Insufficiency and Why?, Reviews in Cardiovascular Medicine, 2003, pp. S2-S6, vol. 4, Supp. 1.

McDonagh et al., Biochemical Detection of Left-Ventricular Systolic Dysfunction, The Lancet, Jan. 3, 1998, p. 9-13, vol. 351.

McGeoch et al., Plasma Brain Natriuretic Peptide After Long-Term Treatment for Heart Failure in General Practice, The European Journal of Heart Failure, 2002, pp. 479-483, vol. 4, Elsevier Science B.V.

Michener et al., Proteolytic Processing of Atriopeptin Prohormone, Molecular Pharmacology, Dec. 1986, pp. 552-557, vol. 30, No. 6, Am. Society for Pharmacology and Experimental Therateutics.

Moe et al., Neurohormonal Activation in Severe Heart Failure: Relations to Patient Death and the Effect of Treatment with Flosequinan, American Heart Journal, Apr. 2000, pp. 587-595, vol. 139, No. 4.

Mukoyama et al., Increased Human Brain Natriuretic Peptide in Congestive Heart Failure, The New England Journal of Medicine, Sep. 13, 1990, pp. 757-758, vol. 323, No. 11, Massachusetts Medical Society.

Nagaya et al., Plasma Brain natriuretic Peptide as a Prognostic Indicator in Patients with Primary Pulmonary Hypertension, Circulation, Aug. 22, 2000, pp. 865-870, vol. 102.

Naghavi et al., From Vulnerable Plaque to Vulnerable Patient; A Call for New Definitions and Risk Assessment Strategies: Part I, Circulation, Oct. 7, 2003, pp. 1664-1672, vol. 108.

Naghavi et al., From Vulnerable Plaque to Vulnerable Patient; A Call for New Definitions and Risk Assessment Strategies: Part II, Circulation, Oct. 14, 2003, pp. 1772-1778, vol. 108.

Needleman et al., Atriopeptins as Cardiac Hormones, Hypertension, Jul.-Aug. 1985, p. 469-482, vol. 7, No. 4.

Ni C.Y., Cardiac Troponin I: A Biomarker for Detection and Risk Stratification of Minor Myocardial Damage, Clin. Lab. 2001, pp. 483-492, vol. 47, No. 9-10.

Nicholls et al., Plasma Cardiac Natriuretic Peptide Levels in Screening for Cardiac Disease, The American Journal of Medicine, Apr. 15, 2004, pp. 561-563, vol. 116.

Nicholls, et al., Brain Natriuretic Peptide-Guided Therapy for Heart Failure, Ann. Med., 2001, pp. 422-427, vol. 33.

Nolan et al., Prospective Study of Heart Rate Variability and Mortality in Chronic Heart Failure, Oct. 13, 1998, pp. 1510-1516, vol. 98.

Ogawa et al., Characterization of Natriuretic Peptide Production by Adult Heart Atria, A. J. Physiol vol. 276 (Heart Circ. Physiol. 45):H1977-86 (1999).

Ogawa et al., Molecular Biology and Biochemistry of Natriuretic Peptide Family, Clinical and Experimental Pharmacology and Physiology, Jan. 1995, pp. 49-53, vol. 22, No. 1, Blackwell Science.

Omland et al., Plasma Brain Natriuretic Peptide as an Indicator of Left Ventricular Systolic Function and Long-term Survival After Acute Myocardial Infarction, Circulation, Jun. 1, 1996, pp. 1963-1969, vol. 93, No. 11.

Omland et al., N-Terminal Pro-brain Natriuretic Peptide is An Independent Predictor of Survival in Patients with Non-ST-Segment Elevation Acute Coronary Syndromes: a TIMI 11B Substudy, Journal of the European Society of Cardiology, Sep. 2001, p. 608, vol. 22.

Pagano F., Marcatorl Cardiaci All' "European Meeting on Biomarkers of Organ Damage and Dysfunction" (EMBODY 2000), Riv. Med. Lab.—JLM., Oct.-Dec. 2000, pp. 72-73, vol. 1, No. 4.

Palmer et al., Angiotensin-Converting Enzyme Gene Polymorphism Interacts With Left Ventricular Ejection Fraction and Brain Natriuretic Peptide Levels to Predict Mortality After Myocardial Infarction, J. Am. Coll. Cardiol., Mar. 5, 2003, pp. 729-736, vol. 41, No. 5, Elsevier Science, Inc.

Pratt et al., Exploration of the Precision of Classifying Sudden Cardiac Death, Circulation, Feb. 1, 1996, pp. 519-524, vol. 93, No. 3.

Prickett et al., Identification of Amino-Terminal Pro-C-Type Natriuretic Peptide in Human Plasma, Biochemical and Biophysical Research Communications, 2001, pp. 519-517, vol. 286, No. 3.

Rademaker et al., Cardiac Natriuretic Peptides for Cardiac Health, Clinical Science Immediate Publication, Oct. 12, 2004, pp. 1-35.

Ricchiuti et al., Cardiac Troponin T Isoforms Expressed in Renal Diseased Skeletal Muscle Will Not Cause False-Positive Results by the Second Generation Cardiac Troponin T Assay by Boehringer Mannheim, Clinical Chemistry, 1998, pp. 1919-1924, vol. 44, No. 9.

Richards et al., Plasma N-Terminal Pro-Brain Natriuretic Peptide and Adrenomedullin; New Neurohormonal Predictors of Left Ventricular Function and Prognosis After Myocardial Infarction, May 19, 1998, pp. 1921-1929, vol. 97.

Richards A.M., The Natriuretic Peptides in Heart Failure, Basic Res. Cardiol., 2004, pp. 94-100, vol. 99, No. 2.

Richards et al., B-Type Natriuretic Peptides and Ejection Fraction for Prognosis After Myocardial Infarction, Circulation, Jun. 10, 2003, pp. 2786-2792, vol. 107.

Richards et al., Neuroendocrine Prediction of Left Ventricular Function and Heart Failure After Acute Myocardial Infarction, Heart, 1999, pp. 114-120, vol. 81.

Richards et al., BNP in Hormone-Guided Treatment of Heart Failure, Trends in Endocrinology & Metabolism, May/Jun. 2002, pp. 151-155, vol. 13, No. 4.

Richards et al., Clinical Applications of B-Type Natriuretic Peptides, Trends in Endocrinology & Metabolism, May 2004, pp. 170-174, vol. 15, No. 4, Elsevier.

Sabatine et al., Multimarker Approach to Risk Strtification in Non-ST Elevation Acute Coronary Syndromes, Circulation, Apr. 16, 2002, pp. 1760-1763, vol. 105.

Sagnella et al., Atrial Natriuretic Peptide in Human Plasma—Comparison of Radioreceptor Versus Radioimmunoassay, Clinica Chimica Acta, Jun. 30, 1987, pp. 37-44, vol. 166, No. 1, Elsevier.

Saito et al., Brain Natriuretic Peptide is a Novel Cardiac Hormone, Biochemical and Biophysical and Biophysical Research Communications, Jan. 31, 1989, pp. 360-368, vol. 158, No. 2.

Clinical Practice Guidelines for Chronic Kidney Disease: Evaluation, Classification, and Stratification, Amer. J. Kidney Diseases, Feb. 2002, pp. S46-S110, vol. 39, No. 2, Supp. 1.

Selvais et al., Cardiac Natriuretic Peptides for Diagnosis and Risk Stratification in Heart Failure: Influences of Left Ventricular Dysfunction and Coronary Artery Disease on Cardiac Hormonal Activation, European Journal of Clinical Investigation, 1998, pp. 636-642, vol. 28.

Selvais et al., Direct Comparison Between Endothelin- 1, N-Terminal Proatrial Natriuretic Factor, and Brain Natriuretic Peptide as Prognostic Markers of Survival in Congestive Heart Failure, Journal of Cardiac Failure, Sep. 2000, pp. 201-207, vol. 6, No. 3.

Selvin S., Statistical analysis of Epidemiologic Data, Monographs i Epidemiology and Biostatistics, 1991, pp. 226 and 230, vol. 17, Oxford University Press, Inc.

Smith et al., Delayed Metabolism of Human Brain Natriuretic Peptide Reflects Resistance to Neutral Endopeptidase, Journal of Endocrinology, 2000, pp. 239-246, vol. 167, Society for Endocrinology, Great Britain.

Stein et al., Natriuretic Peptides: Physiology, Therapeutic Potential, and Risk Stratification in Ischemic Heart Disease, American Heart Journal, May 1998, pp. 914-923, vol. 135, No. 5, Part 1.

Sudoh et al., A New Natriuretic Peptide in Porcine Brian, Nature, Mar. 3, 1988, pp. 78-81, vol. 332, No. 6159.

Sundsfjord et al., Identification and Plasma Concentrations of the N-Terminal Fragment of Proatrial Natriuretic Factor in Man, J Clin Endocrinol Metab, Mar. 1988, pp. 605-610, vol. 66, No. 3.

Takase, Myocardial Micro-Damage in Acute Heart Failure, Journal of Submicroscopic Cytology and Pathology, Jul. 2000, p. 379, Abstract A161, vol. 32, No. 3.

Takemura et al., Venticular Expression of Atrial and Brain Natriuretic Peptides in Patients with Myocarditis, International Journal of Cardiology, 1995, pp. 213-222, vol. 52.

Takemura et al., Expression of Atrial and Brain Natriuretic Peptides and Their Genes in Hearts of Patients with Cardiac Amyloidosis, J. Am. Coll. Cardiol., Mar. 15, 1998, pp. 754-765, vol. 31, No. 4, Elsevier Science Inc.

Talwar et al., Profile of Plasma N-Terminal proBNP Following Acute Myocardial Infarction; Correlation with Left Ventricular Systolic Dysfunction, Eur. Heart J., Sep. 2000, pp. 1514-1521, vol. 21, No. 18.

Tanaka et al., Cellular Localization and Structural Characterization of Natriuretic Peptide-Expressing Ventricular Myocytes from Patients with Dilated Cardiomyopathy, Journal of Histochemistry and Cytochemistry, 1994, pp. 1207-1214, vol. 42, No. 9, USA.

The Joint European Society of Cardiology/American College of Cardiology Committee, Consensus Document, Myocardial Infarction Redefined—A Consensus Document of The Joint European Society of Cardiology/American College of Cardiology Committee for the Redefinition of Myocardial Infarction, Eur. Heart J., Sep. 2000, pp. 1502-1513, vol. 21, No. 18.

Troughton et al., Plasma B-Type Natriuretic Peptide Levels in Systolic Heart Failure, J. Am. Coll. Cardiol., Feb. 4, 2004, pp.416-422, vol. 43, No. 3, Elsevier Inc.

Villar-Palasi et al., Glycogen Metabolism and Glycolytic Enzymes, Annual Review of Biochemistry, 1970, pp. 639-672, vol. 39.

Villarreal et al., Effects of Meclofenamale on the Renin Response to Aortic Constriction in the Rat, American Journal of Physiology, Sep. 1984, pp. R546-R551, Part 2 of Two Parts, vol. 247, No. 3, The American Physiological Society.

Wei et al., Pathophysiologic Concentrations of Human Brain natriuretic Peptide Have Functionally Important Biological Actions in Vivo, JASN, Sep. 1991, p. 422, Abstract 73P, vol. 2, No. 3.

Willging et al., Specificity of Cardiac Troponins I and T in Renal Disease, Clin. Chem. Lab. Med., 1998, pp. 87-92, vol. 36, No. 2.

Wright et al., Amino-Terminal Pro-C-Type Natriuretic Peptide in Heart Failure, Hypertension, Jan. 2004, p. 94-100, vol. 43.

Wright et al., Plasma Amino-terminal Pro-Brain Natriuretic Peptide and accuracy of Heart-Failure Diagnosis in Primary Care, J. Am. Coll. Cardiol., Nov. 19, 2003, pp. 1793-1800, vol. 42, No. 10, Elsevier Inc.

Wu A.H.B., Analytical and Clinical Evaluation of New Diagnostic Tests for Myocardial Damage, Clinica Chimica Acta, 1998, pp. 11-21, vol. 272, Elsevier.

Yandle et al., Brain Natriuretic Peptide—Its Function and Diagnostic Application, Clin. Biochemist. Rev., Feb. 2002, pp. 3-21, vol. 23.

Yasue et al., Localization and Mechanism of Secretion of B-Type Natriuretic Peptide in Comparison with Those of A-Type Natriuretic Peptide in Normal Subjects and Patients with Heart Failure, circulation, Jul. 1994, pp. 195-203, vol. 90, No. 1.

Yoshimura et al., Interaction on Metabolic Clearance Between A-type and B-type Natriuretic Peptides in Patients with Heart Failure, Metabolism, Sep. 2000, pp. 1228-1233, vol. 49, No. 9.

Yoshimura et al., Responses of Plasma Concentrations of A Type Natriuretic Peptide and B Type Natriuretic Peptide to Alacepril, an Angiotensin-Converting Enzyme Inhibitor, in Patients with Congestive Heart Failure, Br. Heart. J., 1994, pp. 528-533, vol. 72.

Yu et al., Plasma Brain natriuretic Peptide—An Independent Predictor of Cardiovascular Mortality in Acute Heart Failure, Eur. J. Heart Fail., 1999, pp. 59-65, vol. 1.

Zanolla et al., Selection of Endpoints for Heart Failure Clinical Trials, Eur. J. Heart Fail., 2003, pp. 717-723, vol. 5, Elsevier B.V.

Ziebig et al., Renal Elimination of Troponin T and Troponin I, Clinical Chemistry, 2003, pp. 1191-1193, vol. 49, No. 7.

Ziesche et al., Interobserver Discordance in the Classification of Mechanisms of Death in Studies of Heart Failure, Journal of Cardiac Failure, Mar. 1995, pp. 127-132, vol. 1, No. 2.

Zoccali et al., Cardiac Natriuretic Peptides are Related to Left Ventricular Mass and Function and Predict Mortality in Dialysis Patients, J. Am. Soc. Nephrol., 2001, pp. 1508-1515, Vol. 12.

Harter et al., Caspase-3 activity is present in cerebrospinal fluid from patients with traumatic brain injury. Journal of Neuroimmunology, 121:76-78, 2001.

International Search Report and the Written Opinion of the International Searching Authority from PCT Application No. PCT/US04/12024.

Cassin et al., *E realizzabile una strategia operative piu efficace per la gestione in urgenza del paziente con dolore toracico acuto?*, Ital Heart J Suppl, Feb. 2000, pp. 186-201, vol. 1.

Futterman et al., *Novel Markers in the Acute Coronary Syndrome: BNP, IL-6, PAPP-A*, American Journal of Critical Care, Mar. 2002, pp. 168-172, vol. 11, No. 2.

Hunt et al., *Immunoreactive amino-terminal pro-brain natriuretic peptide (NT-PROBNP): a new marker of cardicac impairment*, Clinical Endocrinology, 1997, pp. 287-296, vol. 47.

Sagnella et al., *Measurement and significance of circulating Natriuretic peptides in cardiovascular disease*Clinical Science, Nov. 1998, pp. 519-529, vol. 95, No. 5.

Sonel et al., Prospective Study Correlating Fibrinopeptide A, Troponin I, Myoglobin, and Myosin Light Chain Levels with Early and Late Ischemic Events in Consecutive Patients Presenting to the Emergency Department with Chest Pain, Circulation, Sep. 5, 2000, pp. 1107-1113, vol. 102, No. 10.

*ACC/AHA Guidelines for the Management of Patients With ST-Elevation Myocardial Infarction*, Section 2.3, p. e8.

*ACC/AHA 2002 Guideline Update for the Management of Patients With Unstable Angina Non-ST-Segment Elevation Myocardial Infarction*, "Overview of Acute Coronary Syndrome," pp. 4 and 20.

American College of Cardiology and the Joint European Society of Cardiology, *J. Am. Coll. Cardiol.* 36: 959-969 (2000), Albert et al., section entitled "II. Clinical Presentation," p. 960.

Goetze et al., "Quantification of pro-B-type natriuretic peptide and its products in human plasma by use of an analysis independent of precursor processing," *Clin. Chem.* 48:1035-42, 2002.

Hassan et al., "Non-viable myocardium, documented by TL-201 SPECT, is a main determinant of the increase in the secretion of cardiac natriuretic peptides" Medecine Nucleaire, 2000, 24/6, pp. 301-310 (Database EMBASE Accession No. 2001129199 and English language translation).

Omland et al., N-terminal Pro-B-Type natriuretic peptide and long-term mortality in acute coronary syndrome. *Circulation* 106: 2913-18 (2002).

Rabbani, Editorials, "Acute coronary syndromes-Beyond Myocyte necrosis." *N. Engl. J. Med.* 345: 1057-59 (2001).

Sagnella, "Measurement and importance of plasma brain natriuretic peptide and related peptides," *Ann. Clin. Biochem.* 38: 83-93, 2001.

Shimizu et al., "Degradation of human brain natriuretic peptide (BNP) by contact activation of blood coagulation system," *Clin. Chim. Acta* 305: 181-6, 2001.

Silver et al., "BNP Consensus Panel 2004: A Clinical Approach for the Diagnostic, Prognostic, Screening, Treatment Monitoring, and Therapeutic Roles of Natriuretic Peptides in Cardiovascular Disease," *CHF* 10[5 Suppl. 3]: 1-30 (2004).

* cited by examiner

Adjusted 10-month Mortality

USE OF B-TYPE NATRIURETIC PEPTIDE AS A PROGNOSTIC INDICATOR IN ACUTE CORONARY SYNDROMES

INTRODUCTION

The present invention relates in part to methods, compositions, and devices for the measurement of BNP, and the use of such measurement in the diagnosis, prognosis, and treatment of patients with acute coronary syndromes.

BACKGROUND OF THE INVENTION

The following discussion of the background of the invention is merely provided to aid the reader in understanding the invention and is not admitted to describe or constitute prior art to the present invention.

The term "acute coronary syndromes" ("ACS") has been applied to a group of coronary disorders that result from ischemic insult to the heart. Patients with ACS form a heterogeneous group, with differences in pathophysiology, clinical presentation, and risk for adverse events. Such patients present to the physician with conditions that span a continuum that includes unstable angina, non-ST-elevation non-Q wave myocardial infarction ("NST"-"MI"), ST-elevation non-Q wave MI, and transmural (Q-wave) MI. ACS is believed to result largely from thrombus deposition and growth within one or more coronary arteries, resulting in a partial or complete occlusion of the artery, and frequently involves rupture of the plaque, resulting in an ischemic injury. ACS may also be precipitated by a coronary vasospasm or increased myocardial demand. For review, see, e.g., Davies, *Clin. Cardiol.* 20 (Supp. I): 12–17 (1997).

The seriousness of ACS is underlined by the morbidity and mortality that follow the ischemic insult. For example, workers have estimated that within four to six weeks of presentation with ACS, the risk of death or a subsequent MI is 8–14%, and the rate of death, MI, or refractory ischemia is 15–25%. Theroux and Fuster, *Circulation* 97: 1195–1206 (1998) Given that the total number of deaths in the U.S. from acute MI is about 600,000, the search within the art for information that relates to the diagnosis, prognosis, and management of ACS has understandably been extensive. Several potential markers that may provide such information in certain patient populations have been identified, including circulating cardiac troponin levels (see, e.g., Antman et al., *N. Eng. J. Med.* 335: 1342–9 (1996); see also U.S. Pat. Nos. 6,147,688, 6,156,521, 5,947,124, and 5,795,725, each of which is hereby incorporated by reference in its entirety), ST-segment depression (see, e.g., Savonitto et al., *JAMA* 281: 707–13 (1999)), circulating creatine kinase levels (see, e.g., Alexander et al., *Circulation* (Suppl.) 1629 (1998)), and circulating c-reactive protein levels (see, e.g., Morrow et al., *J. Am. Coll. Cardiol.* 31: 1460–5 (1998)).

B-type natriuretic peptide ("BNP" or "BNP-32") is a 32-amino acid neurohormone that is synthesized in ventricular myocardium and released into the circulation in response to ventricular dilation and pressure overload. The functions of BNP, like atrial natriuretic peptide, include natriuresis, vasodilation, inhibition of the renin-angiotensin-aldosterone axis, and inhibition of sympathetic nerve activity. The plasma concentration of BNP is elevated among patients with congestive heart failure (CHF), and increases in proportion to the degree of left ventricular dysfunction and the severity of CHF symptoms. For review, see, e.g., Wiese et al., *Circulation* 102: 3074–9 (2000); Yasue et al., *Circulation* 90: 195–203 (1994); Yoshimura et al., *Circulation* 87: 464–9 (1993); Stein and Levin, *Am. Heart J.* 135: 914–23 (1998); and Omland et al., *Heart* 76: 232–7 (1996).

The precursor to BNP is synthesized as a 108-amino acid molecule, referred to as "pre pro BNP," that is proteolytically processed into a 76-amino acid N-terminal peptide (amino acids 1–76), referred to as "NT pro BNP" and the 32-amino acid mature hormone, referred to as BNP or BNP 32 (amino acids 77–108). It has been suggested that each of these species—NT pro-BNP, BNP-32, and the pre pro BNP—can circulate in human plasma. See, e.g., Tateyama et al., *Biochem. Biophys. Res. Commun.* 185: 760–7 (1992); Hunt et al., *Biochem. Biophys. Res. Commun.* 214: 1175–83 (1995). Pre pro BNP and NT pro BNP, and peptides which are derived from BNP, pre pro BNP and NT pro BNP that are present in the blood as a result of proteolyses of BNP, NT pro BNP and pre pro BNP, are collectively described herein as "markers related to or associated with BNP."

Following the onset of acute MI, the plasma concentration of BNP has been shown to rise rapidly over the first 24 hours, and then to stabilize; patients with large infarcts may have a second peak in BNP concentration several days later. The concentration of BNP, when measured between 1 and 4 days following a transmural infarct, can provide prognostic information that is independent of the left ventricular ejection fraction (LVEF) and other important baseline variables. See, e.g., Talwar et al., *Eur. Heart J.* 21: 1514–21 (2000); Darbar et al., *Am. J Cardiol.* 78: 284–7 (1996); Richards et al., *Heart* 81: 114–20 (1999); Omland et al., *Circulation* 93: 1963–9 (1996); Arakawa et al., *J. Am. Coll. Cardiol.* 27: 1656–61 (1996); and Richards et al., *Circulation* 97: 1921–9 (1998).

To date, however, studies evaluating the prognostic implications of increased BNP concentration have been limited to patients with ST-elevation MI, and few data are available with regard to the prognostic implications of BNP following non ST-elevation acute coronary syndromes, including unstable angina and NST-MI. Thus, there remains in the art the need to identify markers useful in evaluating patient prognosis across the entire spectrum of acute coronary syndromes, so that patients at risk of near-term morbidity or and/or death or can be identified and treated.

SUMMARY OF THE INVENTION

The present invention relates to materials and procedures for evaluating the prognosis of patients suffering from acute coronary syndromes. In particular, the level of BNP in a patient sample, alone or in combination with one or more additional prognostic markers, can provide prognostic information useful for predicting near-term morbidity and/or mortality across the entire spectrum of acute coronary syndromes.

In various aspects, the invention relates to materials and procedures for identifying BNP levels, and/or levels of one or more markers related to BNP, that are associated with an increased predisposition to an adverse outcome in a patient; identifying one or more additional prognostic markers that increase the predictive value of a BNP level, or of a marker related to BNP, for such an adverse outcome; using the BNP level, or the level of a marker related to BNP, in a patient, alone or in combination with one or more additional prognostic markers, to determine a patient's prognosis; and using the BNP level, or the level of a marker related to BNP, in a patient, alone or in combination with one or more additional prognostic markers to determine a treatment regimen that improves a patient's prognosis.

Thus, the materials and procedures described herein can be used to identify those patients that are at acute risk for one or more serious complications, including the risk of death, resulting from acute coronary syndromes, and to guide the clinician in treatment of such patients.

In a first aspect, the invention relates to methods for determining the prognosis of a patient diagnosed with an acute coronary syndrome. These methods comprise identifying a BNP level, or the level of a marker related to BNP, that is associated with an increased predisposition of an adverse outcome resulting from an acute coronary syndrome. Once such a prognostic level is determined, the level of BNP or a related marker, in a patient sample can be measured, and then compared to the prognostic level that is associated with the increased predisposition of the adverse outcome. By correlating the patient level to the prognostic level, the prognosis of the patient can be determined.

The term "BNP" as used herein refers to the mature 32-amino acid BNP molecule itself. As described herein, levels of BNP in patient samples can provide an important prognostic indication of future morbidity and mortality in patients presenting with ACS. As the skilled artisan will recognize, however, other markers related to BNP may also serve as prognostic indicators in such patients. For example, BNP is synthesized as a 108-amino acid pre pro-BNP molecule that is proteolytically processed into a 76-amino acid "NT pro BNP" and the 32-amino acid BNP molecule. Because of its relationship to BNP, the concentration of NT pro-BNP molecule can also provide prognostic information in patients. See, e.g., Fischer et al., *Clin. Chem.* 47: 591–594 (2001); Berger et al., *J. Heart Lung Transplant.* 20: 251-(2001).

The phrase "marker related to BNP" refers to any polypeptide that originates from the pre pro-BNP molecule, other than the 32-amino acid BNP molecule itself. Thus, a marker related to or associated with BNP includes the NT pro-BNP molecule, the pro domain, a fragment of BNP that is smaller than the entire 32-amino acid sequence, a fragment of pre pro-BNP other than BNP, and a fragment of the pro domain. One skilled in the art will also recognize that the circulation contains proteases which can proteolyze BNP and BNP related molecules and that these proteolyzed molecules (peptides) are also considered to be "BNP related" and are additionally subjects of this invention.

The phrase "determining the prognosis" as used herein refers to methods by which the skilled artisan can predict the course or outcome of a condition in a patient. The term "prognosis" does not refer to the ability to predict the course or outcome of a condition with 100% accuracy, or even that a given course or outcome is more likely to occur than not. Instead, the skilled artisan will understand that the term "prognosis" refers to an increased probability that a certain course or outcome will occur; that is, that a course or outcome is more likely to occur in a patient exhibiting a given characteristic, such as the presence or level of a prognostic indicator, when compared to those individuals not exhibiting the characteristic. For example, as described hereinafter, an ACS patient exhibiting a plasma BNP level greater than 80 pg/mL may be more likely to suffer from an adverse outcome than an ACS patient exhibiting a lower plasma BNP level. For example, in individuals not exhibiting the condition, the chance of a certain course or outcome may be 3%. In such a case, the increased probability that the course or outcome will occur would be any number greater than 3%. In preferred embodiments, a prognosis is about a 5% chance of a given outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, and about a 95% chance. The term "about" in this context refers to +/−1%.

A prognosis is often determined by examining one or more "prognostic indicators." These are markers, the presence or amount of which in a patient (or a sample obtained from the patient) signal a probability that a given course or outcome will occur. For example, preferred prognostic indicators in the present invention are BNP and markers related to BNP. As discussed herein, BNP is present in patients suffering from various acute coronary syndromes. When BNP reaches a sufficiently high level in samples obtained from such patients, the BNP level signals that the patient is at an increased probability for morbidity or death, in comparison to a similar patient exhibiting a lower BNP level. A level of a prognostic indicator, such as BNP or a marker related to BNP, that signals an increased probability for morbidity or death is referred to as being "associated with an increased predisposition to an adverse outcome" in a patient.

The skilled artisan will understand that associating a prognostic indicator with a predisposition to an adverse outcome is a statistical analysis. For example, a BNP, or BNP-associated marker, level of greater than 80 pg/mL may signal that a patient is more likely to suffer from an adverse outcome than patients with a level less than or equal to 80 pg/mL, as determined by a level of statistical significance. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001. Exemplary statistical tests for associating a prognostic indicator with a predisposition to an adverse outcome are described hereinafter.

The term "correlating," as used herein in reference to the use of prognostic indicators to determine a prognosis, refers to comparing the presence or amount of the prognostic indicator in a patient to its presence or amount in persons known to suffer from, or known to be at risk of, a given condition; or in persons known to be free of a given condition. For example, a BNP level in a patient can be compared to a level known to be associated with an increased disposition for an MI or death. The patient's BNP level is said to have been correlated with a prognosis; that is, the skilled artisan can use the patient's BNP level to determine the likelihood that the patient is at risk for an MI or death, and respond accordingly. Alternatively, the patient's BNP level can be compared to a BNP level known to be associated with a good outcome (e.g., no MI, no death, etc.), and determine if the patient's prognosis is predisposed to the good outcome.

In certain embodiments, a prognostic indicator is correlated to a patient prognosis by merely its presence or absence. For example, the presence or absence of ST-segment depression in an electrocardiogram can be correlated with a predisposition to certain conditions. See, e.g., Savonitto et al., *JAMA* 281: 707–13 (1999).

In other embodiments, a threshold level of a prognostic indicator can be established, and the level of the indicator in a patient sample can simply be compared to the threshold level. For example, a BNP level of 80 or 100 pg/mL in a patient sample can be established as a level at which a patient is at an increased disposition for morbidity or death. A preferred threshold level for BNP or a BNP-associated marker of the invention is about 25 pg/mL, about 50 pg/mL, about 75 pg/mL, about 100 pg/mL, about 150 pg/mL, about 200 pg/mL, about 300 pg/mL, about 400 pg/mL, about 500 pg/mL, about 600 pg/mL, about 750 pg/mL, about 1000 pg/mL, and about 2500 pg/mL. The term "about" in this context refers to +/−10%.

In yet other embodiments, a "nomogram" can be established, by which a level of a prognostic indicator can be directly related to an associated disposition towards a given outcome. The skilled artisan is acquainted with the use of such nomograms to relate two numeric values.

The phrase "acute coronary syndromes" as used herein refers to a group of coronary disorders that result from ischemic insult to the heart. ACS includes unstable angina, non-ST-elevation non-Q wave MI, ST-elevation non-Q wave MI, and transmural (Q-wave) MI. ACS can be divided into non-ST-elevation ACS and ST-elevation ACS, each of which may be associated with certain prognostic indicators and prognoses, as described herein. The phrase "non-ST-elevation acute coronary syndrome" refers to those ACS not associated with an elevated ST component in an electrocardiogram. Non-ST-elevation ACS include unstable angina and non-ST-elevation non-Q wave MI. See, e.g., Nyman et al., Very early risk stratification by electrocardiogram at rest in men with suspected unstable coronary heart disease. The RISC Study Group, *J. Intern. Med.* 1993; 234: 293–301 (1993); Patel et al., Early continuous ST segment monitoring in unstable angina: prognostic value additional to the clinical characteristics and the admission electrocardiogram, *Heart* 75: 222–28 (1996); Patel et al., Long-term prognosis in unstable angina. The importance of early risk stratification using continuous ST segment monitoring, *Eur. Heart J.* 19: 240–49 (1998); and Lloyd-Jones et al., Electrocardiographic and clinical predictors of acute myocardial infarction in patients with unstable angina pectoris, *Am. J Cardiol.* 81: 1182–86 (1998), each of which is hereby incorporated by reference in its entirety.

Diagnosis of ACS generally, and non-ST-elevation ACS in particular, is well known to the skilled artisan. See, e.g., Braunwald et al., Unstable angina: diagnosis and management, Clinical practice guideline no. 10 (amended), AHCPR publication no. 94–0602. Rockville, Md.: Department of Health and Human Services, (1994); Yusuf et al., Variations between countries in invasive cardiac procedures and outcomes in patients with suspected unstable angina or myocardial infarction without ST elevation-OASIS (Organisation to Assess Strategies for Ischaemic Syndromes) Registry Investigators, *Lancet* 352:507–514 (1998); Savonitto et al., Prognostic value of the admission electrocardiogram in acute coronary syndromes, *JAMA* 281:707–713 (1999); Klootwijk and Hamm, Acute coronary syndromes: diagnosis, *Lancet* 353 (suppl II): 10–15 (1999), each of which is hereby incorporated by reference in its entirety.

The phrase "adverse outcome" as used herein refers to morbidity or mortality suffered by a patient subsequent to the onset of ACS in the patient. For example, a patient may present to a clinician with ACS; an adverse outcome could be a subsequent MI, subsequent onset of angina, subsequent onset of congestive heart failure, or subsequent death. An adverse outcome is said to occur within the "near term" if it occurs within about 10 months of the onset of ACS.

In certain embodiments, one or more additional prognostic indicators can be combined with a level of BNP, or a related marker, in a patient sample to increase the predictive value of BNP or the related marker as a prognostic indicator. The phrase "increases the predictive value" refers to the ability of two or more combined prognostic indicators to improve the ability to predict a given outcome, in comparison to a prediction obtained from any of the prognostic indicators alone. For example, a BNP level of X pg/mL may predict a 10% chance of a subsequent MI in the patient; and a cardiac troponin I level of Y ng/mL may predict a 5% chance of a subsequent MI. But the presence of both a BNP level of X pg/mL and a cardiac troponin I level of Y ng/mL in sample(s) obtained from the same patient may indicate a much higher chance of a subsequent MI in the patient. Preferred additional prognostic indicators of the invention are circulating cardiac-specific troponin levels, ST-segment depression, circulating creatine kinase levels, and circulating c-reactive protein levels.

The skilled artisan will understand that the plurality of prognostic indicators need not be determined in the same sample, or even at the same time. For example, one prognostic indicator may not appear in serum samples until some time has passed from the onset of ACS. Nevertheless, combining, for example, a cardiac troponin I level taken at 1 hour with a BNP level obtained at 48 hours, may provide the skilled artisan with an increased predictive value in comparison to either measurement alone.

Additionally, the increased predictive value need not be an increased probability of an adverse outcome. For example, a cardiac troponin I level taken at 1 hour may indicate a 5% chance of a subsequent MI. But when combined with a later BNP level that indicates a good prognosis in the patient, the result may be to reduce the predicted chance that the patient will suffer a subsequent MI.

The skilled artisan will also understand that a plurality of prognostic indicators may also include both a BNP level and the levels of one or more markers related to BNP; or, alternatively, may be two or more different markers related to BNP. For example, the levels of BNP and NT pro-BNP may be combined to determine the prognosis of a patient with an increased predictive value in comparison to either measurement alone.

The phrase "cardiac-specific troponin" refers to cardiac-specific isoforms of troponin I and T, and/or to complexes comprising at least one cardiac-specific troponin isoform. See, e.g., U.S. Pat. Nos. 6,147,688, 6,156,521, 5,947,124, and 5,795,725, each of which is hereby incorporated by reference in its entirety. Particularly preferred are methods that combine BNP and one or more cardiac-specific troponin isoforms as prognostic markers to determine the prognosis of a patient.

The term "patient sample" refers to a sample obtained from a living person for the purpose of diagnosis, prognosis, or evaluation. In certain embodiments, such a sample may be obtained for the purpose of determining the outcome of an ongoing condition or the effect of a treatment regimen on a condition. Preferred patient samples are blood samples, serum samples, plasma samples, cerebrospinal fluid, and urine samples.

In another aspect, the invention relates to methods for determining a prognostic panel comprising a plurality of prognostic markers that can be used to determine the prognosis of a patient diagnosed with an acute coronary syndrome. These methods preferably comprise identifying a level of BNP, or a marker related to BNP, that is associated with an increased predisposition of an adverse outcome resulting from an acute coronary syndrome, and identifying one or more additional prognostic markers that increase the predictive value in comparison to that obtained from the use of BNP or the related marker alone as a prognostic indicator.

Once the plurality of markers has been determined, the levels of the various markers making up the panel can be measured in one or more patient sample(s), and then compared to the diagnostic levels determined for each marker, as described above.

In yet another aspect, the invention relates to methods for determining a treatment regimen for use in a patient diagnosed with an acute coronary syndrome. The methods preferably comprise determining a level of one or more prognostic markers as described herein, and using the prognostic markers to determine a prognosis for a patient. One or more treatment regimens that improve the patient's prognosis by reducing the increased disposition for an adverse outcome associated with the acute coronary syndrome can then be used to treat the patient.

In a further aspect, the invention relates to kits for determining the prognosis of a patient diagnosed with an acute coronary syndrome. These kits preferably comprise devices and reagents for measuring a BNP level, or the level of a marker related to BNP, in a patient sample, and instructions for performing the assay. Optionally, the kits may contain one or more means for converting a BNP or related marker level to a prognosis. Additionally, the kits may provide devices and reagents for determining one or more additional prognostic markers to be combined with a level of BNP, or a marker related to BNP, in a patient sample.

DETAILED DESCRIPTION OF THE PREFERRED EMBODIMENTS

Figure 1:
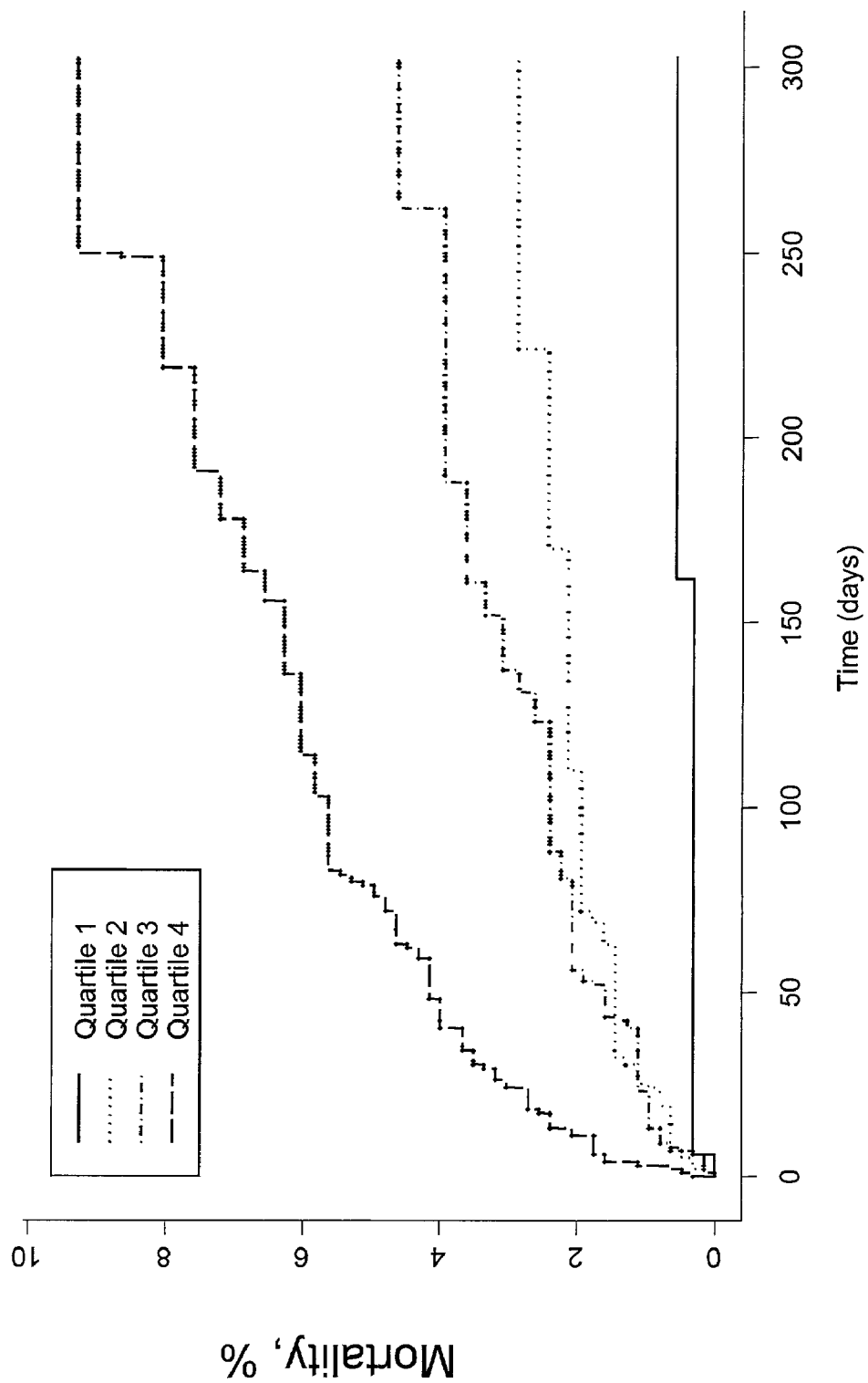
FIG. 1 shows Kaplan-Meier curves relating BNP concentration to 10-month mortality. Patients were divided into quartiles based on the concentration of BNP at enrollment.

Use of BNP as a Prognostic Marker in ACS

As demonstrated herein, the concentration of BNP, measured in the first few days after an acute coronary event, predicts the risk for morbidity and mortality across the entire spectrum of acute coronary syndromes. The prognostic utility of BNP persists after adjusting for clinical evidence of heart failure, as well as other important predictors of mortality, including clinical characteristics, ECG changes and cardiac troponin I.

Previous cohort studies have demonstrated that following acute MI, higher plasma concentrations of BNP and the N-terminal fragment of its prohormone (NT-pro BNP) are associated with larger infarct size (Arakawa et al., *Cardiology* 85: 334–40 (1994); Horio et al., *Am. Heart J.* 126: 293–9 (1993)), adverse ventricular remodeling (Nagaya et al., *Am. Heart J.* 135: 21–8 (1998)), and lower ejection fraction and an increased risk for the development of congestive heart failure and death (Talwar et al., *Eur. Heart J.* 21: 1514–21 (2000); Darbar et al., *Am. J. Cardiol.* 78: 284–7 (1996); Richards et al., *Heart* 81: 114–20 (1999); Omland et al., *Circulation* 93: 1963–9 (1996); Arakawa et al., *J. Am. Coll. Cardiol.* 27: 1656–61 (1996); Richards et al., *Circulation* 97: 1921–9 (1998)). These prior studies have each included fewer than 150 patients, and focused on relatively homogenous groups of patients with ST elevation MI. The following exemplary embodiments extend these findings in patients with non-ST elevation acute coronary syndromes, including unstable angina.

As demonstrated herein, a single measurement of BNP, performed a median of 40 hours after the onset of ischemic symptoms, provides powerful risk-stratification across the entire spectrum of acute coronary syndromes. The prognostic implications of BNP levels are distinct from those of myocyte necrosis; that is, even among patients with unstable angina, the degree of BNP elevation is of prognostic significance.

Moreover, even after correcting for variables such as history of hypertension, heart failure, and prior diuretic or ACE inhibitor use, BNP remained predictive of long-term mortality. Thus, despite heterogeneity in pathophysiology and clinical presentation between patients with ST elevation MI, non-ST elevation ACS, and unstable angina, increasing BNP concentration was predictive of mortality in each of these subgroups, suggesting that activation of the cardiac neurohormonal system may be a unifying feature among patients at high risk for death across the entire spectrum of acute coronary syndromes.

The association between BNP and long-term mortality was independent of clinical evidence of congestive heart failure, as well as cardiac Troponin I, ECG changes, and other known predictors of mortality in ACS. In fact, BNP appeared to be a more powerful predictor of long-term mortality than any other variable measured. In addition, higher BNP levels were associated with an increased risk for the development of nonfatal endpoints, including new or progressive heart failure and myocardial infarction. Finally, it appears that a BNP threshold of 80 to 100 pg/mL, indicative of neurohormonal activation in patients with congestive heart failure, also performs well among patients with ACS.

Also, unlike traditional cardiac biomarkers used to predict risk among patients with ACS, and particularly non-ST elevation ACS, BNP has a putative role in the counter-regulatory response to ischemic injury. As such, it may act as an index of the size or severity of the ischemic insult, as well as the degree of underlying impairment in left ventricular function. For example, in an animal model of transmural myocardial infarction, BNP gene expression was augmented 3-fold in the left ventricle within 4 hours after the onset of coronary artery ligation, and importantly, tissue concentrations of BNP were increased in non-infarcted as well as infarcted regions. Hama et al., *Circulation* 92: 1558–64 (1995). Moreover, it has been demonstrated that BNP increases rapidly, and transiently, following exercise testing in patients with chronic stable angina, and that the degree of BNP elevation is closely correlated with the size of the ischemic territory as measured using nuclear SPECT imaging. Marumoto et al., *Clin. Sci.* (Colch.) 88: 551–6 (1995).

Furthermore, BNP increases transiently following uncomplicated percutaneous transluminal coronary angioplasty even in the absence of changes in pulmonary capillary wedge pressure. Tateishi et al. *Clin. Cardiol.* 23: 776–80 (2000); Kyriakides et al., *Clin. Cardiol.* 23: 285–8 (2000). Several small cross-sectional studies have shown that BNP and Nt-pro BNP concentrations are higher among patients with unstable angina than among patients with stable angina or among healthy controls. Talwar et al., *Heart* 84: 421–4 (2000); Kikuta et al., *Am. Heart J.* 132: 101–7 (1996). In one of these studies (Kikuta et al.), BNP elevation appeared to correlate with echocardiographic findings of regional wall motion abnormalities but not with hemodynamic data obtained at the time of simultaneous cardiac catheterization; furthermore, after medical stabilization, wall motion abnormalities improved and BNP levels fell significantly. Taken together, these prior studies suggest that myocardial ischemia may augment BNP synthesis and release, even in the absence of myocardial necrosis or pre-existing left ventricular dysfunction. Reversible ischemia may lead to a transient increase in left ventricular wall stress, which may be sufficient to cause BNP elevation.

Use of BNP for Determining a Treatment Regimen

A useful prognostic indicator such as BNP can help clinicians select between alternative therapeutic regimens. For example, patients with elevation in cardiac troponin T or I following an acute coronary syndrome appear to derive specific benefit from an early aggressive strategy that includes potent antiplatelet and antithrombotic therapy, and early revascularization. Hamm et al., *N. Engl. J. Med.* 340: 1623–9 (1999); Morrow et al., *J. Am. Coll. Cardiol.* 36: 1812–7 (2000); Cannon et al., *Am. J. Cardiol.* 82: 731–6 (1998). Additionally, patients with elevation in C-reactive protein following myocardial infarction appear to derive particular benefit from HMG-CoA Reductase Inhibitor therapy. Ridker et al., *Circulation* 98: 839–44 (1998). Among patients with congestive heart failure, pilot studies suggest that ACE inhibitors may reduce BNP levels in a dose dependent manner. Van Veldhuisen et al., *J. Am. Coll. Cardiol.* 32: 1811–8 (1998).

Similarly, "tailoring" diuretic and vasodilator therapy based on Nt-pro BNP levels may improve outcomes. Troughton et al., *Lancet* 355: 1126–30 (2000). Finally, in a single pilot study of 16 patients found that randomization to an ACE inhibitor rather than placebo following Q-wave MI was associated with reduced BNP levels over the subsequent 6-month period. Motwani et al., *Lancet* 341: 1109–13 (1993). Because BNP is a counter-regulatory hormone with beneficial cardiac and renal effects, it is likely that a change in BNP concentration reflects improved ventricular function and reduced ventricular wall stress. A recent article demonstrates the correlation of NT pro-BNP and BNP assays (Fischer et al., *Clin. Chem.* 47: 591–594 (2001). It is a further objective of this invention that the concentration of BNP can be used to guide diuretic and vasodilator therapy to improve patient outcome. Additionally, the measurement of one or more markers related to BNP, such as NT-proBNP, for use as a prognostic indicator for patients suffering from acute coronary syndromes, is within the scope of the present invention.

Recent studies in patients hospitalized with congestive heart failure suggest that serial BNP measurements may provide incremental prognositic information as compared to a single measurement; that is, assays can demonstrate an improving prognosis when BNP falls after therapy than when it remains persistently elevated. Cheng et al., *J. Am. Coll. Cardiol.* 37: 386–91 (2001). Thus, serial measurements may increase the prognostic value of a marker in patients with non-ST elevation ACS as well.

Assay Measurement Srategies

Numerous methods and devices are well known to the skilled artisan for measuring the prognostic indicators of the instant invention. With regard to polypeptides, such as BNP, in patient samples, immunoassay devices and methods are often used. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims.

EXAMPLES

The following examples serve to illustrate the present invention. These examples are in no way intended to limit the scope of the invention.

Example 1

Validation of BNP as a Prognostic Indicator in ACS

Stud Population

The Oral Glycoprotein IIb/IIIa Inhibition with Orbofiban in Patients with Unstable Coronary Syndromes (OPUS-TIMI 16) Trial was a randomized multicenter trial comparing an oral glycoprotcin IIb/IIIa inhibitor, orbofiban, with placebo in 10,288 patients with acute coronary syndromes. Patients were included if they presented within 72 hours of the onset of ischemic discomfort and met one or more of the following criteria: dynamic ECG changes (ST deviation $\geq 0.5$ mm, T-mm, T-wave inversion $\geq 3$ mm in $\geq 3$ leads, or left bundle branch block); positive cardiac markers; prior history of coronary artery disease; or age $\geq 65$ with evidence of diabetes or vascular disease. See, e.g., Cannon et al., *Circulation* 102: 149–56 (2000).

The study population described in the Examples herein consisted of a subpopulation of 2525 patients from the OPUS-TIMI 16 study, of whom 825 were enrolled following an index ST elevation MI, 565 following a non-ST elevation MI, and 1133 following a diagnosis of unstable angina. BNP concentration ranged from 0–1456 pg/mL, with a mean of 114±3 pg/mL, a median of 81 pg/mL, and $25^{th}$ and $75^{th}$ percentiles of 44 and 138 pg/mL. Mean time from the onset of ischemic symptoms to randomization was 40±20 hours (median 40 hours).

Blood Sampling

Blood specimens were collected by trained study personnel in citrate tubes and centrifuged for ≧12 minutes. The plasma component was transferred into a sterile cryovial and frozen at −20° C. or colder.

Biochemical Analyses

Troponin I, CKMB, CRP, and BNP were measured using standard immunoassay techniques. These techniques involved the use of antibodies to specifically bind the protein targets. CRP was measured using the N Latex CRP assay (Dade Behring) and fibrinogen was assayed using the Dade Behring Assay on the BN II analyzer. In the case of BNP measurements, an antibody directed against BNP was biotinylated using N-hydroxysuccinimide biotin (NHS-biotin) at a ratio of about 5 NHS-biotin moieties per antibody. The biotinylated antibody was then added to wells of a standard avidin 384 well microtiter plate, and biotinylated antibody not bound to the plate was removed. This formed an anti-BNP solid phase in the microtiter plate. Another anti-BNP antibody was conjugated to alkaline phosphatase using standard techniques, using SMCC and SPDP (Pierce, Rockford, Ill.). The immunoassays were performed on a TECAN Genesis RSP 200/8 Workstation. The plasma samples (10 μL) were pipeted into the microtiter plate wells, and incubated for 60 min. The sample was then removed and the wells were washed with a wash buffer, consisting of 20 mM borate (pH 7.42) containing 150 mM NaCl, 0.1% sodium azide, and 0.02% Tween-20. The alkaline phosphatase-antibody conjugate was then added to the wells and incubated for an additional 60 min, after which time, the antibody conjugate was removed and the wells were washed with a wash buffer. A substrate, (AttoPhos®, Promega, Madison, Wis.) was added to the wells, and the rate of formation of the fluorescent product was related to the concentration of the BNP in the patient samples.

Clinical Endpoints

All-cause mortality and nonfatal myocardial infarction were evaluated through 30 days, and the end of the follow up period (10 months). Myocardial infarction was defined using previously reported criteria based on CKMB elevation (Antman et al., *Circulation* 100: 1593–601 (1999)), and all cases of suspected myocardial infarction were adjudicated by a Clinical Events Committee. The endpoint of new or worsening CHF or cardiogenic shock was collected from case record forms.

Statistical Analyses

Subjects were divided into quartiles based on their concentration of BNP at the time of enrollment in the trial. Means and proportions for baseline variables were compared across quartiles using ANOVA for continuous variables and the $\chi^2$ trend test for categorical variables. The direct correlation between BNP and other continuous baseline variables was assessed using Pearson's test. Mean concentration of BNP was compared between patients who met a study endpoint and those who did not using the Student t test. Cox regression analysis was used to evaluate the association between increasing concentration of BNP and adverse cardiovascular outcomes through 30 days and 10 months. Stratified analyses were performed among patients with a cTnI level>0.1 ng/ml and a cTnI≦0.1 ng/ml, as well as those with and without a clinical diagnosis of congestive heart failure. Subgroup analyses were performed in groups defined by the following index diagnoses: ST elevation MI, non-ST elevation ACS, and unstable angina. Quartile ranges were recalculated for each of these subgroups. For the endpoint of all-cause mortality through the end of follow-up (10 months), a logistic regression model was constructed using forward stepwise selection. Clinical variables that were assessed in >75% of the population were entered into the model, provided they had a univariate p value <0.1; variables were removed from the model if they had a multivariate p value >0.1. Baseline concentrations of cTnI and BNP were then forced into the completed model. Finally, analyses were performed using a BNP threshold of 80 and 100 pg/mL (Dao et al., *J. Am. Coll. Cardiol.* 37: 379–85 (2001)).

Association with Baseline Clinical Variables

In univariate analyses, higher baseline concentration of BNP was associated with older age, female sex, white race, and a prior history of hypertension, congestive heart failure, peripheral vascular disease, and cerebrovascular disease; BNP was inversely associated with history of hypercholesterolemia and current smoking (table 1). As expected, BNP levels were highest among patients with ST elevation MI, intermediate among patients with non-ST elevation MI, and lowest among those with unstable angina (table 1). Patients with higher BNP concentrations were more likely to present in Killip Class II or greater, and were more likely to have ECG changes, elevations in cardiac biomarkers, and renal insufficiency.

TABLE 1

Baseline Clinical Characteristics According to Quartiles of BNP (pg/mL)

| | Quartile 1 | Quartile 2 | Quartile 3 | Quartile 4 | p trend | p Q4 vs Q1 |
|---|---|---|---|---|---|---|
| Range of BNP levels, pg/mL | 0–43.6 | 43.7–81.2 | 81.3–137.8 | 137.9–1456.6 | | |
| n | 631 | 632 | 632 | 630 | | |
| Time to randomization (hrs) | 39 ± 21 | 40 ± 21 | 41 ± 20 | 41 ± 19 | 0.04 | 0.10 |
| Age (years) | 57 ± 10 | 59 ± 11 | 61 ± 12 | 66 ± 11 | <0.0001 | <0.0001 |
| Male | 474 (75%) | 465 (74%) | 472 (75%) | 405 (64%) | 0.0001 | <0.0001 |
| White | 575 (91%) | 592 (94%) | 605 (96%) | 603 (96%) | 0.0002 | 0.001 |
| Past Medical History | | | | | | |
| Hypertension | 246 (39%) | 254 (40%) | 263 (42%) | 298 (47%) | 0.003 | 0.003 |
| Congestive Heart Failure | 26 (4%) | 28 (4%) | 26 (4%) | 56 (9%) | 0.0006 | 0.0008 |

TABLE 1-continued

Baseline Clinical Characteristics According to Quartiles of BNP (pg/mL)

|  | Quartile 1 | Quartile 2 | Quartile 3 | Quartile 4 | p trend | p Q4 vs Q1 |
|---|---|---|---|---|---|---|
| Coronary artery disease | 329 (52%) | 312 (49%) | 294 (47%) | 327 (52%) | 0.7 | 0.9 |
| Peripheral vascular disease | 33 (5%) | 43 (7%) | 48 (8%) | 57 (9%) | 0.008 | 0.009 |
| Cerebrovascular disease | 24 (4%) | 32 (5%) | 39 (6%) | 60 (10%) | <0.0001 | 0.0001 |
| Diabetes | 138 (22%) | 133 (21%) | 132 (21%) | 152 (24%) | 0.4 | 0.3 |
| Hypercholesterolemia | 199 (32%) | 191 (30%) | 173 (28%) | 149 (24%) | 0.0009 | 0.002 |
| Smoking status: |  |  |  |  | 0.0002 | 0.001 |
| Current smoker | 233 (37%) | 263 (42%) | 236 (38%) | 189 (30%) |  |  |
| Never smoker | 193 (31%) | 161 (26%) | 185 (29%) | 254 (40%) |  |  |
| Past smoker | 204 (32%) | 205 (33%) | 209 (33%) | 186 (30%) |  |  |
| Index Diagnosis: |  |  |  |  | <0.0001 | <0.0001 |
| ST elevation MI | 141 (22%) | 189 (30%) | 231 (37%) | 264 (42%) |  |  |
| Non ST elevation MI | 87 (14%) | 137 (22%) | 159 (25%) | 182 (29%) |  |  |
| Unstable angina | 402 (64%) | 306 (48%) | 241 (38%) | 184 (29%) |  |  |
| Physical findings |  |  |  |  |  |  |
| BMI kg/m$^2$ | 29 ± 5 | 28 ± 5 | 28 ± 14 | 28 ± 12 | 0.1 | 0.08 |
| Systolic BP (mm Hg) | 130 ± 20 | 129 ± 19 | 128 ± 22 | 129 ± 21 | 0.3 | 0.4 |
| Killip Class II-IV | 31 (5%) | 36 (6%) | 56 (9%) | 109 (18%) | <0.0001 | <0.0001 |
| Diagnostic Testing |  |  |  |  |  |  |
| Creatinine clearance ≦ 90 | 146 (24%) | 185 (31%) | 229 (38%) | 350 (58%) | <0.0001 | <0.0001 |
| CK-MB > ULN | 212 (58%) | 308 (72%) | 349 (79%) | 388 (86%) | <0.0001 | <0.0001 |
| ST depression ≧ 0.5 mm | 270 (43%) | 297 (47%) | 311 (49%) | 356 (57%) | <0.0001 | <0.0001 |

*CAD = Prior coronary artery disease: previous MI, documented unstable angina, angina pectoris, angiographically confirmed CAD, prior PTCA or CABG not for index event.
MI = myocardial infarction;
BMI = Body Mass Index;
ULN = upper limit of normal Although statistically significant, the associations between the baseline concentration of BNP and C-reactive protein (R=0.2; p<0.0001), Fibrinogen (R=0.18; p<0.0001), peak recorded CK-MB (R=0.09; p=0.0005) and LVEF (R=0.23; p<0.0001) were modest. Results from coronary arteriography, echocardiography, and exercise stress testing were available in a subset of the patient population. Higher BNP concentration was associated with more severe coronary disease, lower ejection fraction, and a positive exercise stress test (p<0.01 for each; table 2).

Clinical Outcomes

Mean concentration of BNP was significantly higher among patients who died by 30 days (p<0.0001) or by 10 months (p<0.0001) vs those who were alive at either time point (table 3). These differences remained significant in subgroups of patients with ST elevation MI, non-ST elevation ACS, and unstable angina (p<0.01 for each subgroup at both 30 days and 10 months; table 4). Mean BNP levels were significantly higher among patients with a myocardial infarction by 30 days (p=0.01) or 10 months (p=0.02), as compared

TABLE 2

Association between cardiac test results and BNP concentration

| Test | 1. Result | n | BNP | BNP (Mean ± SD) | p value |
|---|---|---|---|---|---|
| Coronary Angiography: | None | 103 | 58 [32,111] | 90 ± 104 | <0.0001 |
| No. vessels with ≧ 50% stenosis | 1 | 433 | 73 [41,118] | 92 ± 75 |  |
|  | 2 | 368 | 70 [41,120] | 104 ± 112 |  |
|  | ≧3 | 405 | 93 [49,154] | 136 ± 168 |  |
| LV Ejection Fraction | >50% | 718 | 73 [41,128] | 99 ± 94 | <0.0001 |
|  | ≦50% | 554 | 110 [59,184] | 160 ± 182 |  |
| Stress test | Negative | 374 | 65 [39,106] | 91 ± 95 | 0.003 |
|  | Indeterminate | 118 | 88 [49,143] | 118 ± 128 |  |
|  | Positive | 296 | 88 [44,145] | 118 ± 118 |  |

LV = left ventricular; SD = standard deviation with patients free of MI at these time points (table 3). Finally, BNP concentration was higher among patients who developed new or worsening CHF by 30 days (p<0.0001) or 10 months (p<0.0001) than among those who did not develop CHF,

TABLE 3

Association between baseline BNP concentration (pg/mL) and outcomes

| Outcome | n | Median [25,75] | Mean ± SD | p value* |
|---|---|---|---|---|
| 30 days | | | | |
| Dead | 39 | 153 [79,294] | 226 ± 204 | <0.0001 |
| Alive | 2486 | 80 [43,135] | 113 ± 124 | |
| MI | 70 | 109 [50,159] | 152 ± 159 | 0.02 |
| No MI | 2455 | 80 [44,137] | 113 ± 125 | |
| CHF | 43 | 159 [79,317] | 252 ± 269 | <0.0001 |
| No CHF | 2482 | 80 [43,135] | 112 ± 121 | |
| 10 months | | | | |
| Dead | 85 | 143 [88,308] | 228 ± 228 | <0.0001 |
| Alive | 2440 | 79 [43,133] | 110 ± 120 | |
| MI | 124 | 101 [50,161] | 141 ± 140 | 0.01 |
| No MI | 2401 | 80 [43,134] | 113 ± 126 | |
| CHF | 78 | 158 [82,313] | 256 ± 278 | <0.0001 |
| No CHF | 2447 | 79 [43,133] | 110 ± 116 | |

MI = myocardial infarction; CHF = new or worsening congestive heart failure, or cardiogenic shock; SD = standard deviation; *p value from Wilcoxon Rank Sum Test Unadjusted mortality increased in a stepwise direction across increasing quartiles of baseline BNP concentration (p<0.0001: FIG. 1). These differences remained significant in subgroups of patients with ST elevation MI, non-ST elevation ACS, and unstable angina (p<0.02 for each; FIG. 1). In addition, the relationship between BNP and 10-month outcomes remained graded and significant both among patients with and those without history or exam evidence of CHF at enrollment (table 4).

TABLE 4

Association between baseline BNP concentration (pg/ml) and 10-month outcomes in subgroups based on index diagnosis.

| Outcome | n | Median [25,75] | Mean ± SD | p value* |
|---|---|---|---|---|
| ST elevation MI | 825 | 96 [56,161] | 131 ± 125 | |
| Dead by 30 days | 13 | 153 [77,265] | 236 ± 220 | 0.003 |
| Alive at 30 days | 812 | 95 [56,161] | | |
| Dead by 10 months | 23 | 150 [90,227] | 199 ± 176 | 0.008 |
| Alive at 10 months | 802 | 95 [55,161] | 129 ± 123 | |
| Non-ST elevation MI | 565 | 98 [57,157] | 136 ± 148 | |
| Dead by 30 days | 12 | 176 [149,327] | 265 ± 206 | 0.001 |
| Alive at 30 days | 553 | 97 [56,155] | 134 ± 145 | |
| Dead by 10 months | 28 | 176 [123,322] | 245 ± 176 | <0.0001 |
| Alive at 10 months | 537 | 95 [56,152] | 131 ± 144 | |
| Unstable Angina | 1133 | 60 [33,105] | 92 ± 111 | |
| Dead by 30 days | 14 | 94 [69,237] | 182 ± 195 | 0.02 |
| Alive at 30 days | 1119 | 60 [33,105] | 90 ± 109 | |
| Dead by 10 months | 34 | 96 [70,265] | 233 ± 292 | <0.0001 |
| Alive at 10 months | 1099 | 58 [33,104] | 87 ± 97 | |

Figure 2:
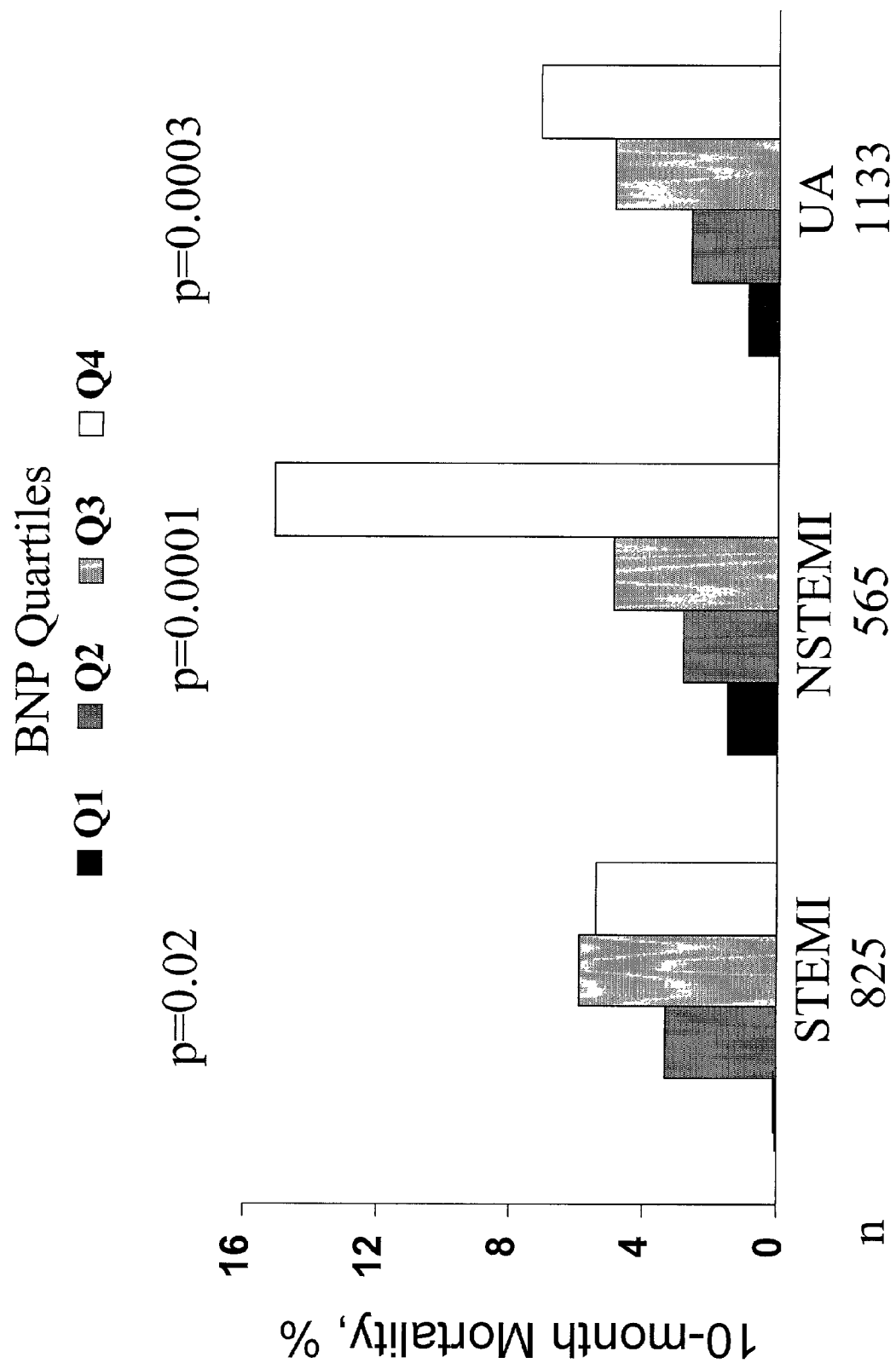
FIG. 2 shows the association between BNP concentration and 10-month mortality. Patients were divided into quartiles based on the concentration of BNP at enrollment. Quartiles were recalibrated for each of the subgroups shown. STEMI=ST elevation myocardial infarction; NSTEMI=non ST elevation myocardial infarction; UA=unstable angina.
Figure 3:
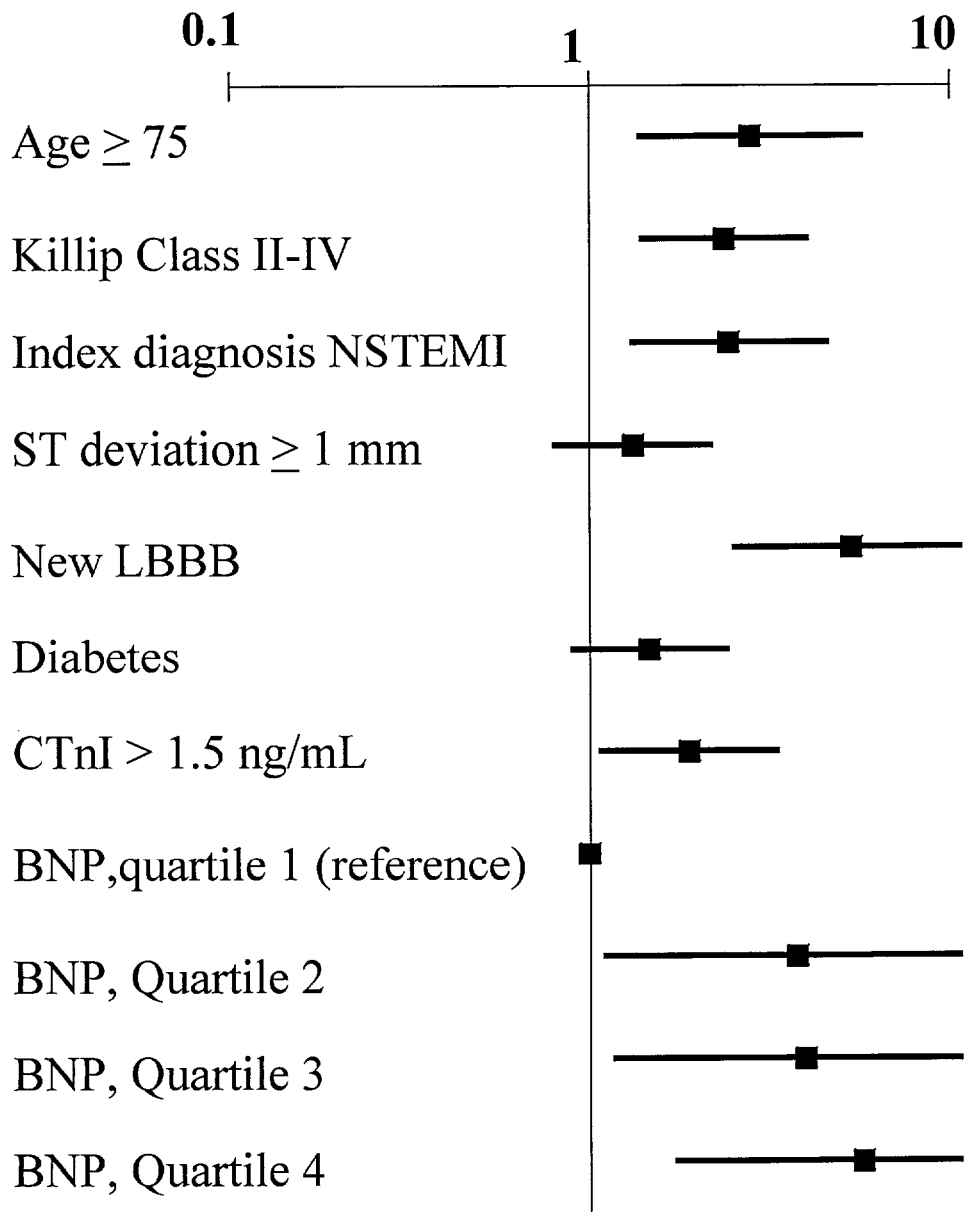
FIG. 3 shows a stepwise logistic regression model showing the relationship between selected baseline clinical variables and 10-month mortality. Cardiac troponin I (cTnI) and BNP quartiles were forced into the final model. Odds ratios and 95% confidence intervals are shown. In addition to the variables shown in the figure, the final model included history of hyperlipidemia or peripheral vascular disease; prior therapy with diuretics, ACE inhibitors, nitrates, or heparin; heart rate; blood pressure; and creatinine clearance.
Figure 4:
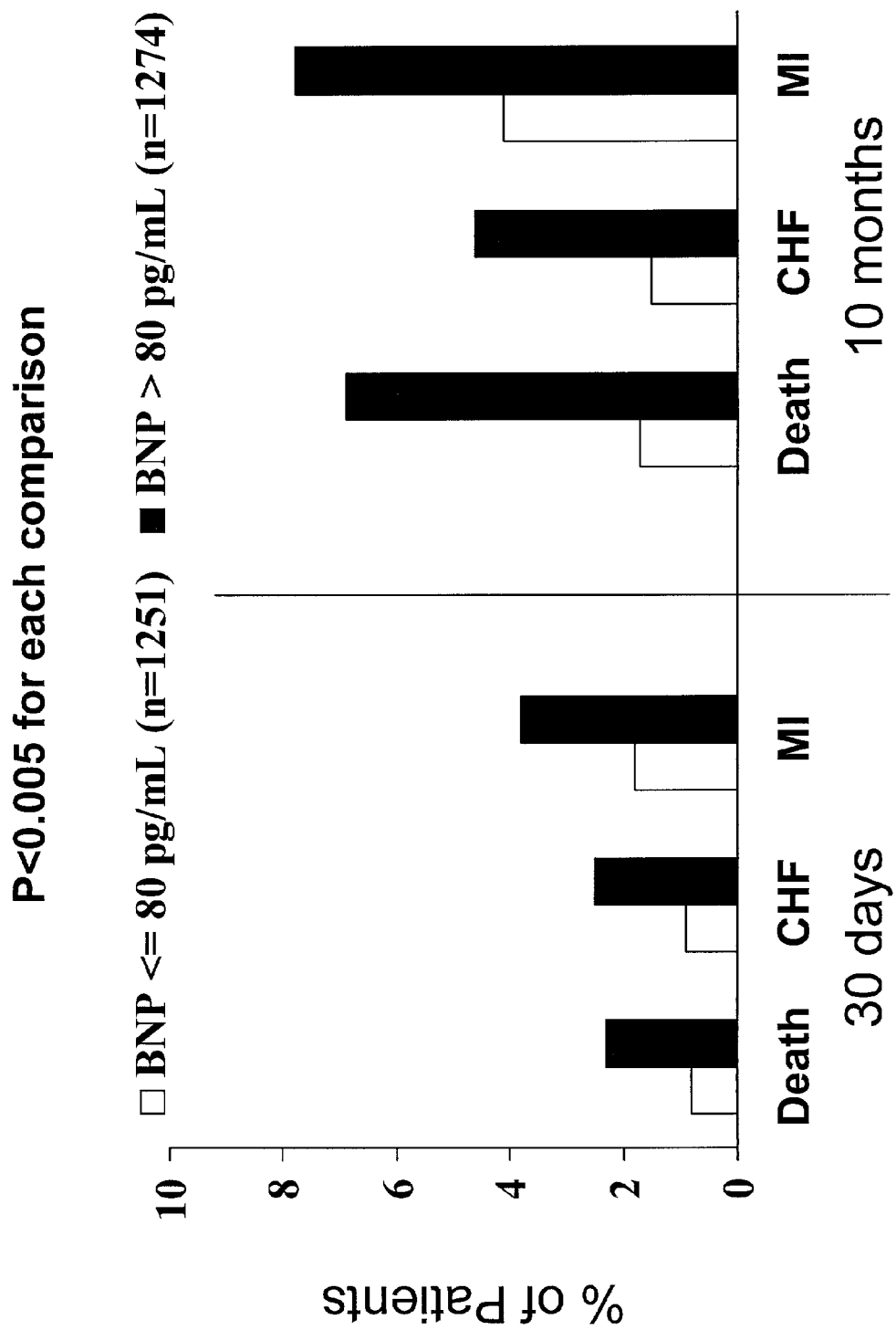
FIG. 4 shows the numbers of patients in 3 adverse outcome groups (death, congestive heart failure (CHF), and myocardial infarction (MI)) at 30 days and 10 months, among patients with a BNP concentration above and below a pre-specified threshold of 80 pg/mL.
Figure 5:
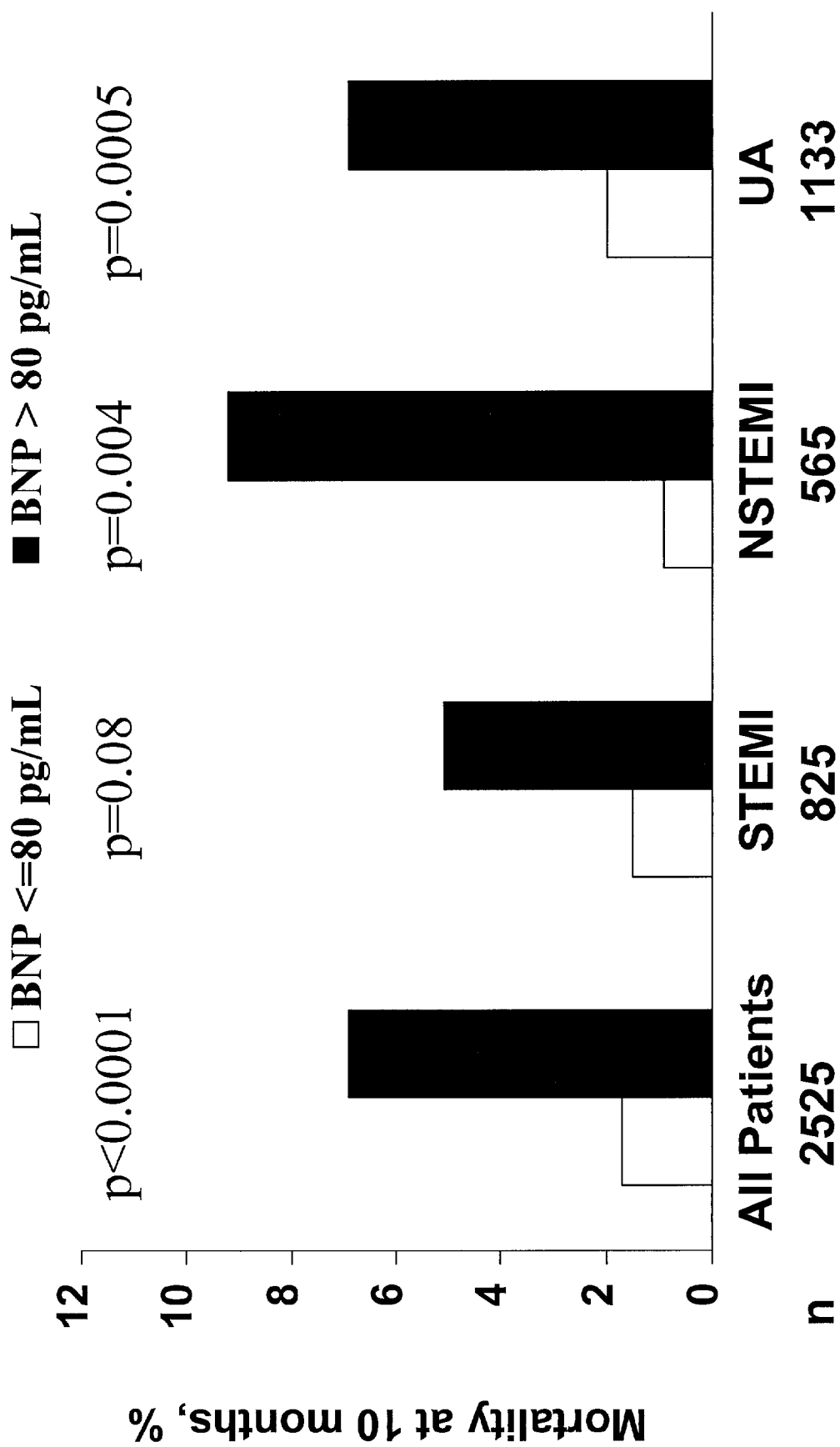
FIG. 5 shows the relationship between BNP concentration and 10-month mortality, using a threshold of 80 pg/mL to define BNP elevation. STEMI=ST elevation myocardial infarction; NSTEMI=non ST elevation myocardial infarction; UA—unstable angina.
Figure 6:
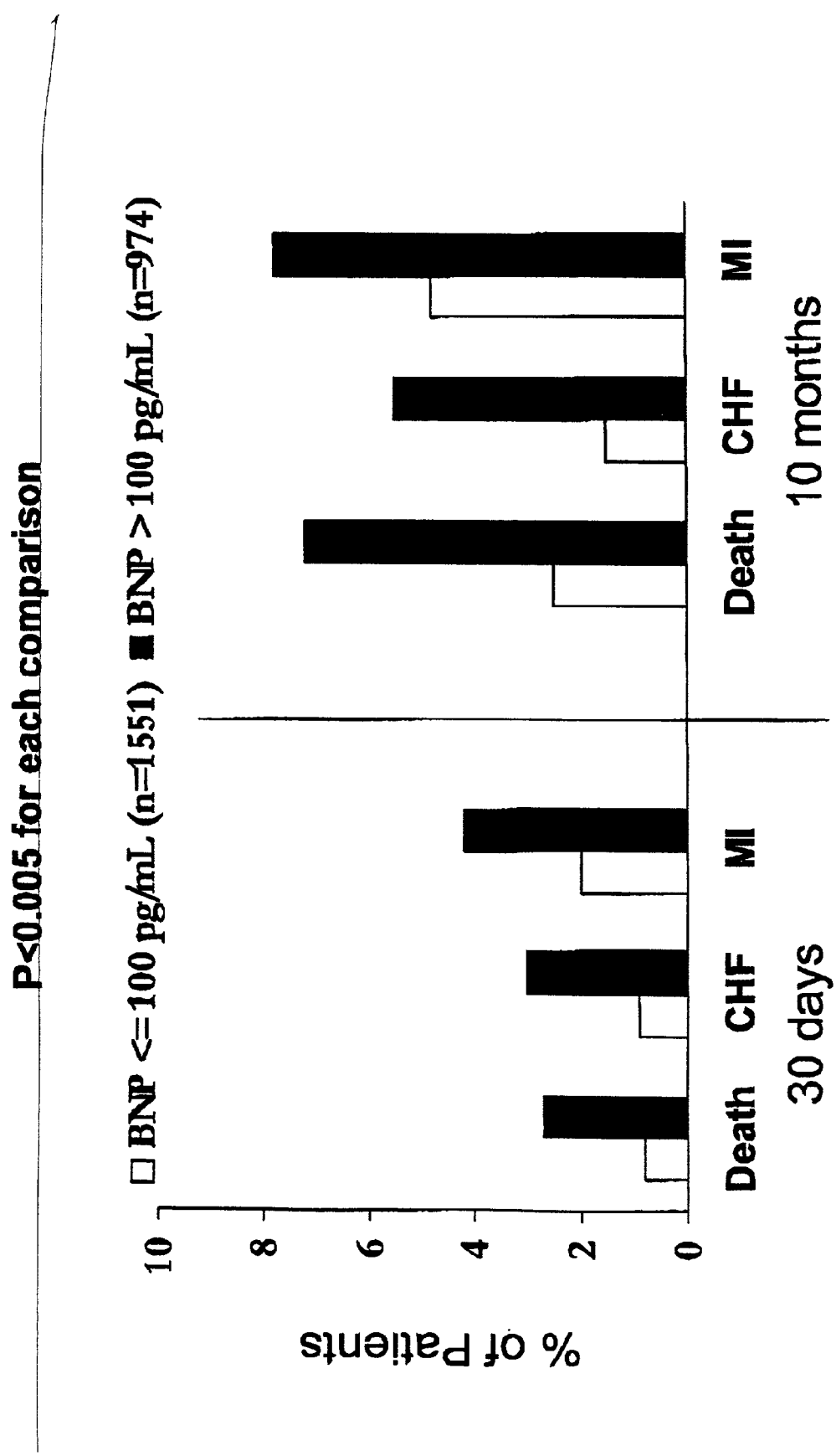
FIG. 6 shows the numbers of patients in 3 adverse outcome groups (death, congestive heart failure (CHF), and myocardial infarction (MI)) at 30 days and 10 months, among patients with a BNP concentration above and below a threshold of 100 pg/mL.
Figure 7:
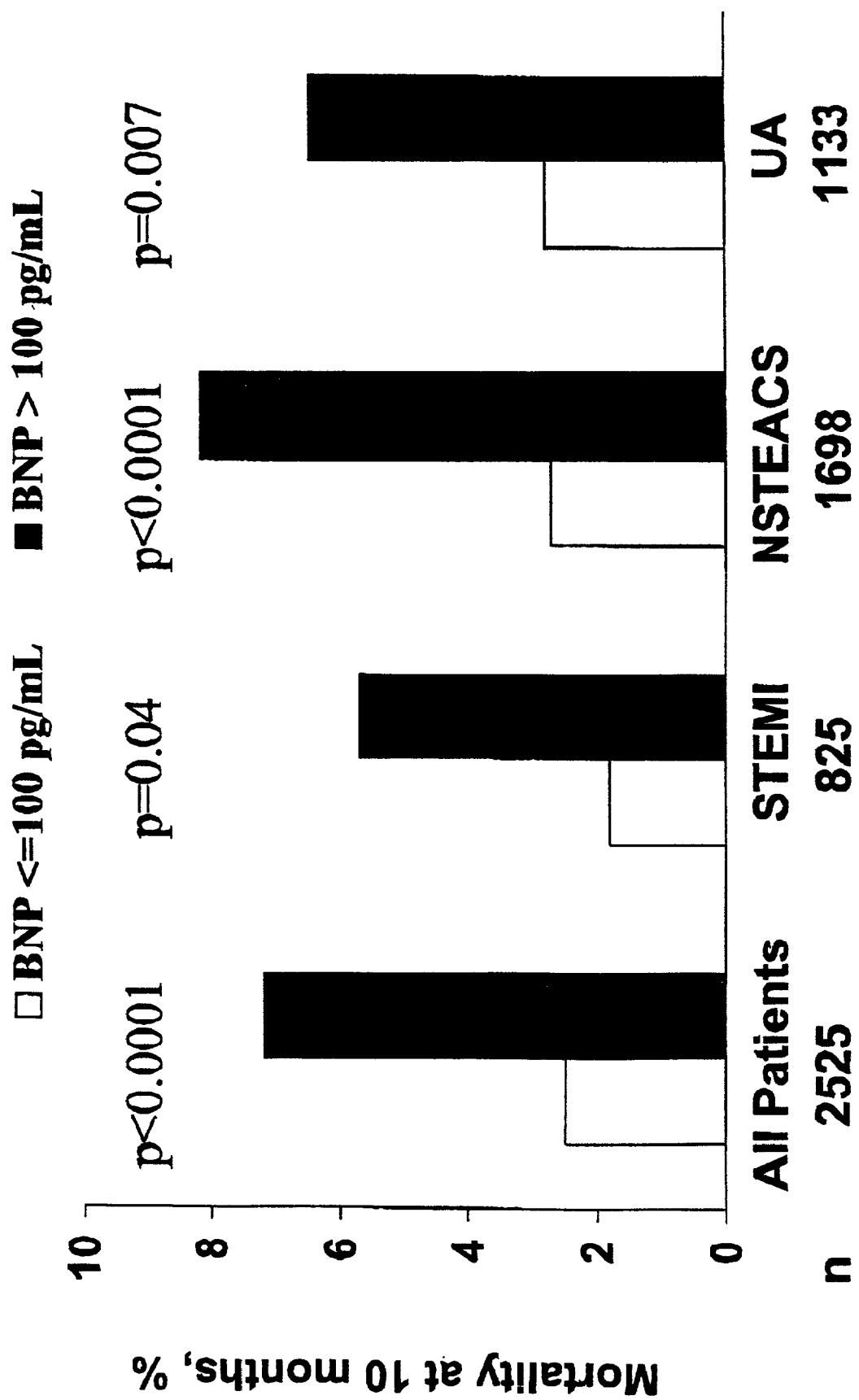
FIG. 7 shows the relationship between BNP concentration and 10-month mortality, using a threshold of 100 pg/mL to define BNP elevation. STEMI=ST elevation myocardial infarction; NSTEACS=non ST elevation acute coronary syndrome; UA—unstable angina.

MI = myocardial infarction; SD = Standard deviation; *p value from Wilcoxon Rank Sum Test When stratification was performed based on the concentration of cTnI at the time of enrollment, increasing BNP concentration remained associated with higher 10-month mortality, both among those with a cTnI<0.1 ng/mL (n=882; p=0.01) and those with a cTnI≧0.1 ng/mL (n—1630; p<0.0001) (FIG. 2). After adjustment for other independent predictors of long-term mortality, including ST deviation and cTnI, increasing concentration of BNP remained associated with a higher rate of death by 10 months (FIG. 3). The adjusted odds ratios for 10-month mortality were 3.9 (1.1–13.6), 4.3 (1.3–15.0), and 6.7 (2.0–22.6) for patients wit concentrations in the second, third, and fourth quartile, respectively (FIG. 3). Evaluation of 80 and 100 pg/mL BNP Threshold Analyses were performed using prospectively defined BNP thresholds of 80 and 100 pg/mL. Patients with a plasma concentration of BNP greater than 80 or 100 pg/mL were significantly more likely to suffer death, myocardial infarction, or new/progressive CHF than those with a BNP level lower than the selected threshold (80 pg/mL threshold: p<0.005 for each at 30 days and 10 months; FIG. 4; 100 pg/mL threshold: p<0.005 for each at 30 days and 10 months; FIG. 6). In subgroups of patients with ST elevation MI, non-ST elevation ACS, and unstable angina, a BNP level greater than either 80 or 100 pg/mL was associated with a significant increase in the risk for 10-month mortality (FIGS. 5 and 7).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for predicting cardiac mortality rate in a patient with an acute coronary syndrome, comprising: drawing a sample of a body fluid from said patient, contacting said sample with a first antibody that specifically binds to a first marker selected from the group consisting of cardiac Troponin-T and cardiac Troponin-I;

contacting said sample with a second antibody that specifically binds to a second marker selected from the group consisting of BNP, NT-proBNP, and pro-BNP;

providing means for determining binding between each of said respective markers and each of said respective antibodies, whereby said binding provides a means for determining cardiac mortality rate.

2. The method of claim 1, wherein said body fluid is selected from the group consisting of blood, serum, plasma, and urine.

3. The method of claim 1, wherein said body fluid is selected from the group consisting of blood, serum, plasma, and urine.

4. A method for predicting cardiac mortality rate in a patient diagnosed with an acute coronary syndrome, comprising: drawing a sample of a body fluid from said patient, contacting said sample with a first antibody that specifically binds to a first marker selected from the group consisting of cardiac Troponin-T and cardiac Troponin-I;

contacting said sample with a second antibody that specifically binds to a second marker selected from the group consisting of BNP, NT-proBNP, and pro-BNP;

providing means for determining binding between each of said respective markers and each of said respective antibodies, whereby said binding provides a means for determining cardiac mortality rate.

5. A method for assigning a prognosis to a patient with an acute coronary syndrome, comprising:

performing an assay on a sample obtained from said patient with a first antibody that specifically binds to a first marker selected from the group consisting of CK-MB, C-reactive protein, cardiac Troponin-T, and cardiac Troponin-I;

performing an assay on said sample with a second antibody that specifically binds to a second marker selected from the group consisting of BNP, NT-proBNP, and pro-BNP;

determining binding between said markers and said respective antibodies; and relating said binding to said prognosis, wherein said prognosis is subsequent myocardial infarction, subsequent onset of angina, subsequent onset of congestive heart failure, or subsequent death.

6. The method of claim 5, wherein said sample is a body fluid is selected from the group consisting of blood, serum, plasma, and urine.

7. A method for assigning a prognosis to a patient diagnosed with an acute coronary syndrome, comprising:

performing an assay on a sample obtained from said patient with a first antibody that specifically binds to a first marker selected from the group consisting of CK-MB, C-reactive protein, cardiac Troponin-T, and cardiac Troponin-I;

performing an assay on said sample with a second antibody that specifically binds to a second marker selected from the group consisting of BNP, NT-proBNP, and pro-BNP;

determining binding between said markers and said respective antibodies; and relating said binding to said prognosis, wherein said prognosis is subsequent myocardial infarction, subsequent onset of angina, subsequent onset of congestive heart failure, or subsequent death.

8. The method of claim 7, wherein said sample is a body fluid selected from the group consisting of blood, serum, plasma, and urine.

\* \* \* \* \*